United States Patent

Nishimura et al.

(10) Patent No.: US 10,463,043 B2
(45) Date of Patent: Nov. 5, 2019

(54) FUNGICIDE COMPOSITION FOR AGRICULTURAL AND HORTICULTURAL USE

(71) Applicant: Nippon Soda Co., Ltd., Chiyoda-ku, Tokyo (JP)

(72) Inventors: Satoshi Nishimura, Odawara (JP); Takayuki Fujii, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 15/762,638

(22) PCT Filed: Oct. 5, 2016

(86) PCT No.: PCT/JP2016/079654
§ 371 (c)(1),
(2) Date: Mar. 23, 2018

(87) PCT Pub. No.: WO2017/061483
PCT Pub. Date: Apr. 13, 2017

(65) Prior Publication Data
US 2018/0271093 A1    Sep. 27, 2018

(30) Foreign Application Priority Data

Oct. 9, 2015    (JP) .................... 2015-201240

(51) Int. Cl.
| | | |
|---|---|---|
| A01N 43/42 | (2006.01) | |
| A01N 43/60 | (2006.01) | |
| A01N 43/72 | (2006.01) | |
| A01N 43/56 | (2006.01) | |
| A01N 43/10 | (2006.01) | |
| A01N 37/22 | (2006.01) | |
| A01N 47/12 | (2006.01) | |
| A01N 43/80 | (2006.01) | |
| A01N 43/54 | (2006.01) | |
| A01N 37/46 | (2006.01) | |
| A01N 43/24 | (2006.01) | |
| A01N 43/40 | (2006.01) | |
| A01N 43/653 | (2006.01) | |
| A01N 43/90 | (2006.01) | |

(52) U.S. Cl.
CPC ............ *A01N 43/42* (2013.01); *A01N 37/22* (2013.01); *A01N 37/46* (2013.01); *A01N 43/10* (2013.01); *A01N 43/24* (2013.01); *A01N 43/40* (2013.01); *A01N 43/54* (2013.01); *A01N 43/56* (2013.01); *A01N 43/60* (2013.01); *A01N 43/653* (2013.01); *A01N 43/72* (2013.01); *A01N 43/80* (2013.01); *A01N 43/90* (2013.01); *A01N 47/12* (2013.01)

(58) Field of Classification Search
CPC ........ A01N 43/42; A01N 43/60; A01N 43/72; A01N 43/56; A01N 43/10; A01N 37/22; A01N 47/12; A01N 43/80; A01N 43/54
See application file for complete search history.

(56) References Cited

U.S. PATENT DOCUMENTS

| 2011/0136782 A1 | 6/2011 | Mitani et al. |
| 2012/0289702 A1 | 11/2012 | Shibayama et al. |
| 2014/0073792 A1 | 3/2014 | Shibayama et al. |
| 2014/0221298 A1 | 8/2014 | Kuwahara |

FOREIGN PATENT DOCUMENTS

| CN | 103889229 A | 6/2014 |
| JP | 2016-199526 A | 12/2016 |
| WO | WO 2010/018686 A1 | 2/2010 |
| WO | WO 2011/081174 A1 | 7/2011 |
| WO | WO 2013/047441 A1 | 4/2013 |
| WO | WO 2014/095994 A1 | 6/2014 |
| WO | WO 2014/130409 A2 | 8/2014 |
| WO | WO 2015/055707 A1 | 4/2015 |
| WO | WO 2015/055752 A1 | 4/2015 |
| WO | WO 2015/055755 A1 | 4/2015 |
| WO | WO 2015/055757 A1 | 4/2015 |
| WO | WO 2015/124542 A1 | 8/2015 |
| WO | WO 2015/141867 A1 | 9/2015 |
| WO | WO 2017/080870 A1 | 5/2017 |
| WO | WO 2017/183664 A1 | 10/2017 |

OTHER PUBLICATIONS

International Search Report dated Dec. 27, 2016, in PCT/JP2016/079654, with English translation.
Office Action dated Sep. 12, 2017, in Taiwan Application No. 105132358, with English translation.
Supplementary European Search Report dated Mar. 1, 2019, in EP 16853637.3.

*Primary Examiner* — Brenda L Coleman
(74) *Attorney, Agent, or Firm* — Foley & Lardner LLP

(57) ABSTRACT

The present invention provides a fungicide composition for agricultural and horticultural use, comprising compound A represented by formula (1) (in formula (1), Xs each independently represents a halogeno group or a C1-6 alkyl group; n represents a number of Xs and is an integer of 0 to 5; X' represents a halogeno group; $R^1$, $R^2$ and $R^3$ each independently represents a C1-6 alkyl group, a C1-6 alkoxy group or a hydroxyl group; $A^1$ and $A^2$ each independently represents a nitrogen atom or a carbon atom), and at least one compound B selected from the group consisting of pydiflumetofen, pyraziflumid, isofetamid, tolprocarb, fluxametamide, broflanilide, tiadinil, fenoxanil and triflumezopyrim.

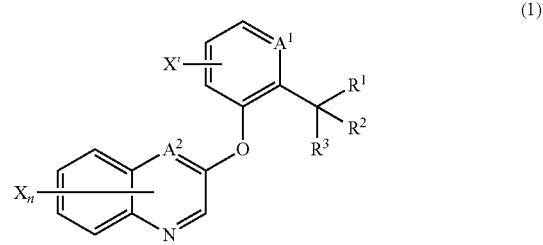

(1)

8 Claims, No Drawings

FUNGICIDE COMPOSITION FOR AGRICULTURAL AND HORTICULTURAL USE

CROSS-REFERENCE TO RELATED APPLICATIONS

This application is a National Stage application of PCT/JP2016/079654, filed Oct. 5, 2016, which claims priority from Japanese application JP 2015-201240, filed Oct. 9, 2015.

TECHNICAL FIELD

The present invention relates to a fungicide composition for agricultural and horticultural use. More specifically, the present invention relates to a fungicide composition for agricultural and horticultural use which exhibits an excellent controlling effect against plant diseases even at a low dosage and is free from concerns about phytotoxicity to useful plants.

Priority is claimed on Japanese Patent Application No. 2015-201240, filed Oct. 9, 2015, the content of which is incorporated herein by reference.

BACKGROUND ART

A lot of chemicals for control of crop diseases is used in cultivation of agricultural and horticultural crops. However, for the reasons such as insufficient control efficacy, restriction of its use due to the appearance of drug-resistant pathogenic fungi, phytotoxicity and contamination to plants, or toxicity to human beings, beasts, fishes and the like, many of them cannot be said to be satisfactory control chemicals.

Under such circumstances, various fungicide compositions containing a nitrogen-containing heterocyclic compound and/or a salt thereof as an active ingredient have been proposed (for example, refer to Patent Documents 1 and 2).

PRIOR ART LITERATURE

Patent Documents

Patent document 1: WO2010/018686
Patent document 2: WO2011/081174

DISCLOSURE OF INVENTION

Problems to be Solved by the Invention

An object of the present invention is to provide a fungicide composition for agricultural and horticultural use which exhibits an excellent controlling effect against plant diseases even at low dosage and is free from concerns about phytotoxicity to useful plants.

Means for Solving the Problems

Intensive researches were conducted to solve the above-mentioned problems. As a result, the present invention including the following aspects has been completed.

That is, the present invention is as follows.

[1] A fungicide composition for agricultural and horticultural use comprising:
at least one compound A selected from the group consisting of a compound represented by formula (1), a compound represented by formula (2), and salts thereof; and
at least one compound B selected from the group consisting of pydiflumetofen, pyraziflumid, isofetamid, tolprocarb, fluxametamide, broflanilide, triflumezopyrim, tiadinil, fenoxanil, N-(5-chloro-2-isopropylbenzyl)-N-cyclopropyl-3-(difluoromethyl)-5-fluoro-1-methyl-1H-pyrazole-4-carboxamide, 4-phenoxybenzyl 2-amino-methyl nicotinate, fenpicoxamid, benzovindiflupyr, mefentrifluconazole, mandestrobin, dichlobentiazox and quinofumelin.

[Chemical formula 1]

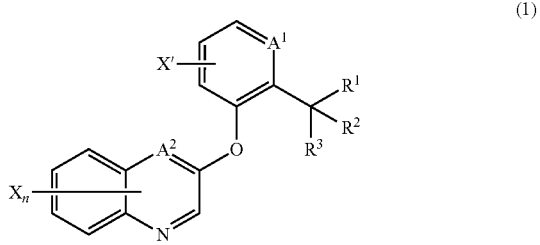

(1)

[in formula (1), Xs each independently represents a halogeno group or a C1-6 alkyl group. n represents a number of Xs and is an integer of 0 to 5. X' represents a halogeno group. $R^1$, $R^2$ and $R^3$ each independently represents a C1-6 alkyl group, a C1-6 alkoxy group or a hydroxyl group. $A^1$ and $A^2$ each independently represents a nitrogen atom or a carbon atom.]

[Chemical formula 2]

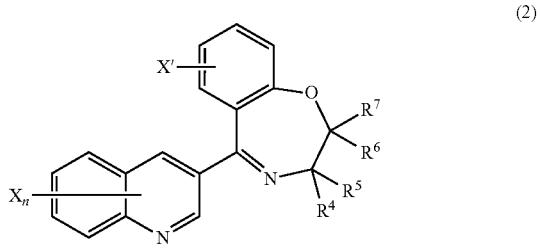

(2)

[in forumula (2), Xs each independently represents a halogeno group or a C1-6 alkyl group. n represents a number of Xs and is an integer of 0 to 6. X' represents a halogeno group. $R^4$, $R^5$, $R^6$ and $R^7$ each independently represents a hydrogen atom, a C1-6 alkyl group or a hydroxyl group.]

[2] The fungicide composition for agricultural and horticultural use according to [1], wherein compound A is a compound represented by formula (a-1).

[Chemical formula 3]

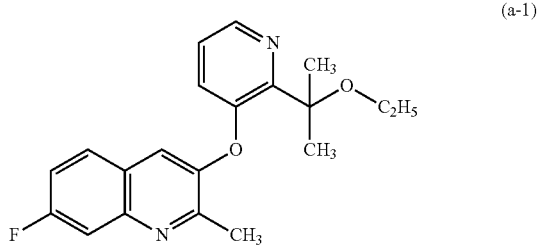 [SMILES: CCOC(C)(C)c1ncccc1Oc1cc2ccc(F)cc2nc1C]

(a-1)

[3] The fungicide composition for agricultural and horticultural use according to [1], wherein compound A is a compound represented by formula (a-2).

[Chemical formula 4]

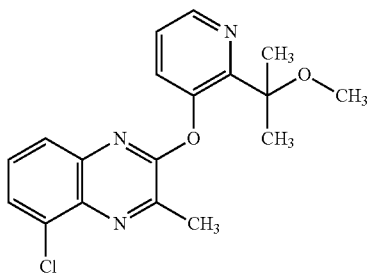

(a-2)

[4] The fungicide composition for agricultural and horticultural use according to [1], wherein compound A is a compound represented by formula (a-3).

[Chemical formula 5]

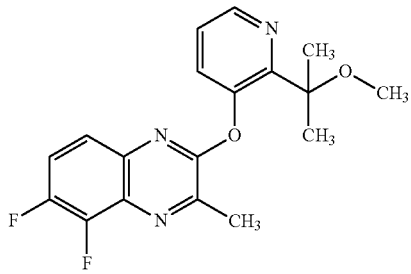

(a-3)

[5] The fungicide composition for agricultural and horticultural use according to [1], wherein compound A is a compound represented by formula (a-4).

[Chemical formula 6]

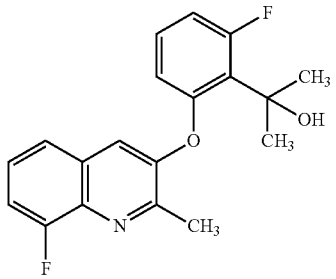

(a-4)

[6] The fungicide composition for agricultural and horticultural use according to [1], wherein compound A is a compound represented by formula (a-5).

[Chemical formula 7]

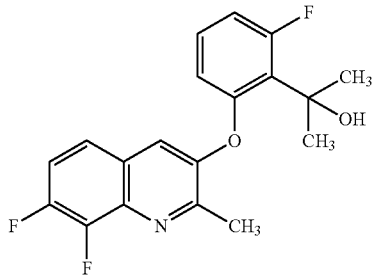

(a-5)

[7] The fungicide composition for agricultural and horticultural use according to [1], wherein compound A is a compound represented by formula (a-6).

[Chemical formula 8]

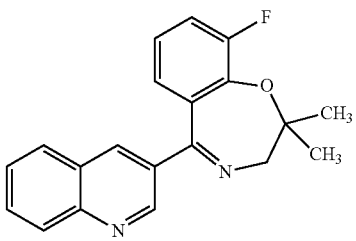

(a-6)

[8] The fungicide composition for agricultural and horticultural use according to any one of [1] to [7], wherein compound B is at least one selected from the group consisting of pyraziflumid, isofetamid, tolprocarb, fluxametamide, broflanilide, triflumezopyrim, tiadinil, fenoxanil, 4-phenoxybenzyl 2-amino-methyl nicotinate, fenpicoxamid, benzovindiflupyr, mefentrifluconazole, mandestrobin and dichlobentiazox.

[9] The fungicide composition for agricultural and horticultural use according to any one of [1] to [7], wherein compound B is at least one selected from the group consisting of pyraziflumid, isofetamid, tolprocarb, fluxametamide, broflanilide, triflumezopyrim, 4-phenoxybenzyl 2-amino-methyl nicotinate, fenpicoxamid, benzovindiflupyr and mefentrifluconazole.

[10] The fungicide composition for agricultural and horticultural use according to any one of [1] to [7], wherein compound B is at least one selected from the group consisting of pyraziflumid, tolprocarb, fluxametamide, triflumezopyrim, 4-phenoxybenzyl 2-amino-methyl nicotinate, fenpicoxamid and benzovindiflupyr.

[11] The fungicide composition for agricultural and horticultural use according to any one of [1] to [7], wherein compound B is at least one selected from the group consisting of pyraziflumid, tolprocarb, 4-phenoxybenzyl 2-amino-methyl nicotinate, fenpicoxamid and benzovindiflupyr.

Effects of the Invention

The fungicide composition for agricultural and horticultural use according to the present invention exhibits an excellent controlling effect against plant diseases even at a very low dosage and is free from concerns about phytotoxicity to useful plants. The fungicide composition for agricultural and horticultural use according to the present invention exhibits a remarkable synergistic plant disease control effect which cannot be predicted from the plant disease control effect obtained when using compound A alone or compound B alone.

BEST MODE FOR CARRYING OUT THE INVENTION

The fungicide composition for agricultural and horticultural use according to the present invention includes compound A and compound B.
(Compound A)
Compound A used in the present invention is at least one selected from the group consisting of a compound represented by formula (1) (hereinafter, sometimes referred to as compound (1)), a compound represented by formula (2) (hereinafter, sometimes referred to as compound (2)), a salt of compound (1), and a salt of compound (2).

Xs in formula (1) or formula (2) independently represents a halogeno group or a C1-6 alkyl group. n represents a number of Xs and is an integer of 0 to 6.

Examples of the C1-6 alkyl group for X include a methyl group, ethyl group, n-propyl group, i-propyl group, n-butyl group, s-butyl group, i-butyl group, t-butyl group, n-pentyl group, n-hexyl group and the like. Some or all of the hydrogen atoms in the C1-6 alkyl group may be substituted with other groups as long as the effects of the present invention are not inhibited. Examples of the substituents include a halogeno group, hydroxyl group and the like.

Examples of the halogeno group for X include a fluoro group, chloro group, bromo group, and iodo group.

X' in formula (1) or formula (2) represents a halogeno group. As the halogeno group for X', the same examples as those exemplified for X can be mentioned.

$R^1$, $R^2$ and $R^3$ in formula (1) each independently represents a C1-6 alkyl group, a C1-6 alkoxy group or a hydroxyl group. As the C1-6 alkyl group for $R^1$, $R^2$ and $R^3$, the same examples as those exemplified for X can be mentioned.

Examples of the C1-6 alkoxy group for $R^1$, $R^2$ and $R^3$ include a methoxy group, ethoxy group, n-propoxy group, i-propoxy group, n-butoxy group, s-butoxy group, i-butoxy group, t-butoxy group and the like.

$R^4$, $R^5$, $R^6$ and $R^7$ in formula (2) each independently represents a hydrogen atom, a C1-6 alkyl group or a hydroxyl group. As the C1-6 alkyl group for $R^4$, $R^5$, $R^6$ and $R^7$, the same examples as those exemplified for X can be mentioned.

The salt of the compound (1) and the salt of the compound (2) used in the present invention are not particularly limited as long as they are agriculturally and horticulturally acceptable salts. For example, a salt of an inorganic acid such as a hydrochloride, nitrate, sulfate, phosphate or the like; a salt of organic acid such as an acetate, lactate, propionate, benzoate or the like; and the like can be mentioned.

Compound (1) and salt thereof are known substances. Specific examples of compound (1) and salt thereof include compounds described in, for example, WO 2011/081174 A1. In addition, compound (1) and salt thereof can be produced by known methods, for example, a method described in WO 2011/081174 A1.

Compound (2) and salt thereof are known substances. Specific examples of compound (2) and salt thereof include compounds described in, for example, WO 2010/018686 A1. In addition, compound (2) and salt thereof can be produced by known methods, for example, a method described in WO 2010/018686 A1.

In the present invention, compound A is preferably a compound represented by any one of formulas (a-1) to (a-6).
(Compound B)

Compound B used in the present invention is at least one selected from the group consisting of pydiflumetofen, pyraziflumid, isofetamid, tolprocarb, fluxametamide, broflanilide, triflumezopyrim, tiadinil, fenoxanil, N-(5-chloro-2-isopropylbenzyl)-N-cyclopropyl-3-(difluoromethyl)-5-fluoro-1-methyl-1H-pyrazole-4-carboxamide (CAS Registry No. 1255734-28-1), 4-phenoxybenzyl 2-amino-methyl nicotinate (CAS Registry No. 1531626-08-0), fenpicoxamid, benzovindiflupyr, mefentrifluconazole, mandestrobin, dichlobentiazox, and quinofumelin.

Among these compound, pyraziflumid, isofetamid, tolprocarb, fluxametamide, broflanilide, triflumezopyrim, tiadinil, fenoxanil, 4-phenoxybenzyl 2-amino-methyl nicotinate (CAS Registry No. 1531626-08-0), fenpicoxamid, benzovindiflupyr, mefentrifluconazole, mandestrobin and dichlobentiazox are preferable; pyraziflumid, isofetamid, tolprocarb, fluxametamide, broflanilide, triflumezopyrim, 4-phenoxybenzyl 2-amino-methyl nicotinate (CAS Registry No. 1531626-08-0), fenpicoxamid, benzovindiflupyr and mefentrifluconazole are more preferable; pyraziflumid, tolprocarb, fluxametamide, triflumezopyrim, 4-phenoxybenzyl 2-amino-methyl nicotinate (CAS Registry No. 1531626-08-0), fenpicoxamid and benzovindiflupyr are even more preferable; and pyraziflumid, tolprocarb, 4-phenoxybenzyl 2-amino-methyl nicotinate (CAS Registry No. 1531626-08-0), fenpicoxamid and benzovindiflupyr are particularly preferable.

In the fungicide composition for agricultural or horticultural use according to the present invention, the weight ratio of compound A and Compound B (compound A:compound B) is usually 1,000:1 to 1:1,000, preferably 100:1 to 1:100, more preferably 20:1 to 1:100, more preferably 1:1 to 1:100, more preferably 1:1 to 1:50, and even more preferably 1:1 to 1:20.

The fungicide composition of the present invention may contain a fertilizer, a solid carrier, a thickener, a surfactant, a spreading agent, an additive, a solvent or the like within a range not affecting the effects of the present invention.

Examples of the fertilizer include compost, oil-cake, fish powder, cow dung, poultry manure etc., and organic materials obtained by processing these fertilizer; nitrogenous fertilizers such as ammonium sulfate, ammonium nitrate, lime nitrate, urea or the like; phosphate fertilizers such as lime perphosphate, primary ammonium phosphate, fused phosphate fertilizer or the like; potash fertilizer such as potassium chloride, potassium sulfate, potassium nitrate or the like; magnesia fertilizer such as magnesia lime or the like; lime fertilizer such as slaked lime or the like; silicate fertilizer such as potassium silicate or the like; boron fertilizer such as borate; chemical fertilizer containing various inorganic fertilizers; and the like.

Examples of the solid carrier include vegetable powders such as soybean particles and wheat flour; mineral fine powders such as silicon dioxide, diatomaceous earth, apatite, gypsum, talc, bentonite, pyrophyllite, clay, joint soil or the like; and the like.

Examples of the additives include organic and inorganic compounds such as sodium benzoate, urea, sodium sulfate decahydrate or the like; rapeseed oil, soybean oil, sunflower oil, castor oil, pine oil, cotton seed oil, derivatives of these oils and concentrations of these oils; and the like.

Examples of the solvent include petroleum fractions such as kerosene, xylene, solvent naphtha or the like; cyclohexane, cyclohexanone, dimethylformamide, dimethyl sulfoxide, alcohol, acetone, methyl isobutyl ketone, mineral oil, vegetable oil, water and the like.

Examples of the surfactant include, for example, nonionic surfactants such as an alkylphenyl ether to which polyoxyethylene is added, alkyl ether to which polyoxyethylene is added, higher fatty acid ester to which polyoxyethylene is added, sorbitan higher fatty acid ester to which polyoxyethylene is added, tristyryl phenyl ether to which polyoxyethylene is added; a sulfate ester salt of alkylphenyl ether to which polyoxyethylene is added, alkyl benzene sulfonate, sulfate salt of higher alcohol, alkyl naphthalene sulfonate, polycarboxylate, lignin sulfonate, formaldehyde condensate of alkyl naphthalene sulfonate, isobutylene-maleic anhydride copolymer, and the like.

The fungicide composition for agricultural and horticultural use according to the present invention may further contain other fungicides, insecticidal/acaricidal agents, synergistic agents and the like as long as the effects of the present invention is not impaired.

Representative examples of other fungicides, insecticides, acaricides and plant growth regulators are shown below.
Fungicide:
(1) Nucleic acid biosynthesis inhibitor:
  (a) RNA polymerase I inhibitor: benalaxyl, benalaxyl-M, furalaxyl, metalaxyl, metalaxyl-M, oxadixyl; clozylacon, ofurace;
  (b) adenosine deaminase inhibitor: bupirimate, dimethirimol, ethirimol;
  (c) DNA/RNA synthesis inhibitor: hymexazol, octhilinone;
  (d) DNA topoisomerase II inhibitor: oxophosphoric acid;
(2) karyokinesis inhibitor and cell division inhibitor:
  (a) β-tubulin polymerization inhibitor: benomyl, carbendazim, chlorfenazole, fuberidazole, thiabendazole; thiophanate, thiophanate-methyl; diethofencarb; zoxamide; ethaboxam;
  (b) cell division inhibitor: pencycuron;
  (c) delocalization inhibitor of spectrin-like protein: fluopicolide;
(3) Respiration inhibitor:
  (a) complex I NADH oxidation-reduction inhibitor: diflumetorim; tolfenpyrad;
  (b) complex II succinic acid dehydrogenase inhibitor: benodanil, flutolanil, mepronil; fluopyram; fenfuram, furmecyclox; carboxin, oxycarboxin; thifluzamide; benzovindiflupyr, bixafen, fluxapyroxad, furametpyr, isopyrazam, penflufen, penthiopyrad, Sedaxan; boscalid;
  (c) complex III ubiquinol oxidase Qo inhibitor: azoxystrobin, coumoxystrobin, coumethoxystrobin, enoxastrobin, flufenoxystrobin, picoxystrobin, pyraoxystrobin; pyraclostrobin, pyrametostrobin, triclopyricarb; kresoxim-methyl, trifloxystrobin; dimoxystrobin, fenaminstrobin, metominostrobin, orysastrobin; famoxadone; fluoxastrobin; fenamidone; pyribencarb;
  (d) complex III ubiquinol reductase Qi inhibitor: cyazofamid; amisulbrom;
  (e) oxidative phosphorylation uncoupling agent: binapacryl, meptyldinocap, dinocap; fluazinam; ferimzone;
  (f) oxidative phosphorylation inhibitor (ATP synthase inhibitor): fenthin acetate, fentin chloride, fentin hydroxide;
  (g) ATP production inhibitor: silthiofam;
  (h) complex III cytochrome bc1 (ubiquinone reductase) Qx (unknown) inhibitor: ametoctradin;
(4) Amino acid and protein synthesis inhibitor
  (a) methionine biosynthesis inhibitor: andoprim, cyprodinil, mepanipyrim, pyrimethanil;
  (b) protein synthesis inhibitor: blasticidin-S; kasugamycin; kasugamycin hydrochloride; streptomycin; oxytetracycline;
(5) Signal transfer inhibitor:
  (a) quinoxyfen, proquinazid;
  (b) MAP/histidine kinase inhibitor in osmotic pressure signal transfer: fenpiconil, fludioxonil; chlozolimate, iprodione, procymidone, vinclozolin;
(6) Lipid and cell membrane synthesis inhibitor:
  (a) phospholipid biosynthesis and methyltransferase inhibitor: edifenphos, iprobenfos, pyrazophos; isoprothiolane;
  (b) lipid peroxide agent: biphenyl, chloroneb, dichloran, quintozene, tecnazene, tolclofos-methyl; etridiazole;
  (c) agents affecting cell membrane: iodocarb, propamocarb, propamocarb hydrochloride, propamocarb-fosetylate, prothiocarb;
  (d) microorganisms disturbing virus cell membrane: *Bacillus subtilis, Bacillus subtilis* strain QST713, *Bacillus subtilis* strain FZB24, *Bacillus subtilis* strain MBI600, *Bacillus subtilis* strain D747;
  (e) agents disturbing cell membrane: *melaleuca alternifolia* (tea tree) extract;
(7) Cell membrane sterol biosynthesis inhibitor:
  (a) C14 position demethylation inhibitor in sterol biosynthesis: triforine; pyrifenox, pyrisoxazole; fenarimol, flurprimidol, nuarimol; imazalil, imazalil-sulphate, oxpoconazole, pefurazoate, prochloraz, triflumizole, viniconazole; azaconazole, bitertanol, bromconazole, cyproconazole, diclobutrazol, difenoconazole, diniconazole, diniconazole-M, epoxyconazole, etaconazole, fenbuconazole, fluquinconazole, flusilazole, flutriafol, furconazole, furconazole-cis, hexaconazole, imibenconazole, ipuconazole, metconazole, myclobutanil, penconazole, propiconazole, quinconazole, simeconazole, tebuconazole, tetraconazole, triadimefon, triadimenol, triticonazole; prothioconazole, voriconazole;
  (b) Δ14 reductase and Δ8→Δ7-isomerase inhibitor in sterol biosynthesis: aldimorph, dodemorph, dodemorph-acetate, fenpropimorph, tridemorph, fenpropidine, piperalin; spiroxamine;
  (c) 3-keto reductase inhibitor in C4 position demethylation in sterol biosynthesis system: fenhexamid; fenpyrazamine;
  (d) squalene epoxidase inhibitor in sterol biosynthesis system: pyributicarb; naftifen, terbinafine;
(8) cell wall synthesis inhibitor
  (a) trehalase inhibitor: validamycin;
  (b) chitin synthetase inhibitor: polyoxins, polyoxorim;
  (c) cellulose synthetase inhibitor: dimethomorph, flumorph, pyrimorph; benthiavalicarb, iprovalicarb, tolprocarb, valifenalate; mandipropamide;
(9) Melanin biosynthesis inhibitor
  (a) reductase inhibitor in melamin biosynthesis: fthalide; pyroquilon; tricyclazole;
  (b) anhydrase inhibitor in melanin biosynthesis: carpropamid; diclocymet; fenoxanil;
(10) Resistance-inducing agent of host plant:
  (a) agents affecting salicylic acid synthetic pathway: acibenzolar-s-methyl;
  (b) others: probenazole; tiadinil; isotianil; laminarin; extract liquid of *Reynoutria sachalinensis*;
(11) agents of which the activity is unknown: cymoxanil, osetyl.aluminum, phosphoric acid (phosphate), tecloftalam, triazoxide, flusulfamide, diclomezine, methasulfocarb, cyflufenamid, metrafenone, pyriofenone, dodine, dodine free base, flutianil;
(12) Agent having multy activities: copper (copper salt), bordeaux mixture, copper hydroxide, copper naphthalate, copper oxide, oxychloride copper, copper sulfate, sulfur, sulfur product, calcium polysulfide; ferbam, mancozeb, maneb, mancopper, metiram, polycarbamate, propineb, thiram, zineb, ziram; captan, captafol, folpet; chlorothalonil; dichlofluanid, tolylfluanid; guazatine, iminoctadine acetate, iminoctadine albesilate; anilazine; dithianon; chinomethionat; fluoroimide;
(13) Other agents: DBEDC, fluor folpet, guazatine acetate, bis (8-quinolinolato) copper (II), propamidine, chloropicrin, cyprofuram, *agrobacterium*, bethoxazin, diphenylamine, methyl isothiocyanate (MITC), mildew-mycin, capsaicin, curfraneb, cyprosulfamide, dazomet, debacarb, dichlorophen, difenzoquat, difenzoquat. methyl sulfonate, flumetover, fosetyl.calcium, fosetyl.sodium, irmamycin, natamycin, nitrothal isopropyl, oxamocarb, puropamocin sodium, pyrrolnitrin, tebufloquin, tolnifanide, zarilamide, algophase, amicarthiazol, oxathiapiprolin, metiram zinc, benthiazole, trichlaamide, uniconazole, mildew-mycin, oxyfenthiin, picarbutrazox;

Insecticides/acaricides, Nematocides, Soil pesticides, (1) Acetylcholine esterase inhibitor:

(a) Carbamate-based: alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, oxamyl, pirimicarb, propoxur, thiodicarb, thiofanox, triazamate, trimethacarb, XMC, xylycarb; fenothiocarb, MIPC, MPMC, MTMC, aldoxycarb, allyxycarb, aminocarb, bufencarb, cloethocarb, metam-sodium, promecarb;

(b) Organic phosphorus-based: acephate, azamethiphos, azinphos-ethyl, azinphos-methyl, cadusafos, chlorethoxyfos, chlorfenvinphos, chlormephos, chlorpyriphos, chlorpyriphos-methyl, coumaphos, cyanophos, demeton-S-methyl, diazinon, dichlorvos/DDVP, dicrotophos, dimethoate, dimethylvinfos, disulfoton, EPN, ethion, ethoprophos, famphur, fenamiphos, fenitrothion, fenthion, fosthiazete, heptenophos, imicyafos, isofenphos, isocarbophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridafenthion, quinalphos, sulfotep, tebupirimfos, temephos, terbufos, tetrachlorvinphos, thiomethon, triazophos, trichlorfon, vamidothion; bromophos-ethyl, BRP, carbophenothion, cyanofenphos, CYAP, demeton-S-methyl sulphone, dialifos, dichlofenthion, dioxabenzofos, etrimfos, fensulfothion, flupyrazofos, fonofos, formothion, fosmethilan, isazophos, iodofenphos, methacrifos, pirimiphos-ethyl, phosphocarb, propaphos, prothoate, sulprofos;

(2) GABA-agonistic chloride ion channel antagonist: chlordane, endosulfan, ethiprole, fipronil, pyrafluprole, pyriprole; camphechlore, heptachlor, dienochlor;

(3) Sodium channel modulator: acrinathrin, d-cis-trans-allethrin, d-trans allethrin, bifenthrin, bioallethrin, bioallethrin β-cyclopentyl isomer, bioresmethrin, cycloprotophosphorus, cycloprothrin, cyfluthrin, β-cyfluthrin, cyhalothrin, λ-cyhalothrin, γ-cyhalothrin, cypermethrin, α-cypermethrin, β-cypermethrin, θ-cypermethrin, ξ-cypermethrin, cyphenothrin [(1R)-trans isomer], δ-methrin, empenthrin [(EZ)-(1R)-isomer], esfenvalerate, ethofenprox, fenpropathrin, fenvalerate, flucythrinate, flumethrin, tau-fluvalinate, halfenprox, imiprothrin, kadethrin, permethrin, phenothrin [(1R)-trans isomer], prallethrin, pyrethrum, resmethrin, silafluofen, tefluthrin, tetramethrin, tetramethrin [(1R)-isomer], tralomethrin, transfluthrin; allethrin, pyrethrin, pyrethrin I, pyrethrin II, profluthrin, dimefluthrin, bioethanomethrin, biopermethrin, transpermethirn, fenfluthrin, fenpirithrin, flubrocythrinate, flufenoprox, metofluthrin, protrifenbute, pyresmethrin, terallethrin;

(4) Nicotinic acetylcholine receptor agonist: acetamiprid, clothianidine, dinotefuran, imidacloprid, nitenpyram, nithiazine, thiacloprid, thiamethoxam, sulfoxaflor, nicotine; flupyradifurone;

(5) Nicotinic acetylcholine receptor allosteric modulator: spinetoram, spinosad;

(6) Chloride channel activator: abamectin, emamectin benzoate, lepimectin, milbemectin; ivermectin, seramectin, doramectin, eprinomectin, moxidectin; milbemycin; milbemycin oxime;

(7) Juvenile hormone-like substances: hydroprene, kinoprene, methoprene, fenoxycarb, pyriproxyfen, diofenolan, epofeneonane, triprene;

(8) Other nonspecific inhibitor: methyl bromide, chloropicrin, sulfuryl fluoride, borax, tartar emetic;

(9) Homoptera selective feeding inhibitor: flonicamid, pymetrozine, pyrifluquinazon;

(10) Acari growth inhibitor: clofentezine, diflovidazin, hexythiazox, etoxazole;

(11) Microorganism-derived insect midgut inner membrane distrupting agent: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*, Bt crop protein: Cry1Ab, Cry1Ac, Cry1Fa, Cry1A.105, Cry2Ab, Vip3A, mCry3A, Cry3Ab, Cry3Bb, Cry34Ab1/Cry35Ab1;

(12) Mitochondria ATP biosynthesis enzyme inhibitor: diafenthiuron, azocyclotin, cyhexitin, fenbutatin oxide, propargite, tetradifon;

(13) Oxidative phosphorylation uncoupling agent: chlorfenapyr, sulfluramid, DNOC; binapacryl, dinobuton, dinocap;

(14) Nicotinic acetylcholine receptor channel blocker: bensultap, cartap hydrochloride; nereistoxin; thiosultap-sodium, thiocyclarm;

(15) Chitin synthesis inhibitor: bistrifluron, chlorfluazuron, diflubenzuron, flucycloxuron, flufenoxuron, hexaflumuron, lufenuron, novaluron, nobifumuron, teflubenzuron, triflumuron, buprofezin, fluazuron;

(16) Diptera molting disturbing agent: cyromazine;

(17) Molting hormone receptor agonist: chromafenozide, halofenozide, methoxyfenozide, tebufenozide;

(18) Octopamine receptor agonist: amitraz, demiditraz, chlordimeform;

(19) Mitochondria electron transfer chain complex III inhibitor: acequinocyl, fluacrypyrim, hydramethylnon;

(20) Mitochondria electron transfer chain complex I inhibitor: fenazaquin, fenproximate, pyrimidifen, pyridaben, tebufenpyrad, tolfenpyrad, rotenone;

(21) Voltage-dependent sodium channel blocker: indoxacarb, metaflumizone;

(22) Acetyl CoA carboxylase inhibitor: spirodiclofen, spiromesifen, spirotetramat;

(23) Mitochondria electron transfer chain complex IV inhibitor: aluminium phosphide, calcium phosphide, phosphine, zinc phosphide, cyanide;

(24) Mitochondria electron transfer chain complex II inhibitor: cyenopyrafen, cyflumetofen, pyflubumide;

(25) Ryanodine receptor modulator: chlorantraniliprole, cyantraniliprole, flubendiamide, cyclaniliprole, tetraniliprole;

(26) Mixed function oxidase inhibitor compound: piperonyl butoxide;

(27) Latrophilin receptor agonist: depsipeptide, cyclodepsipeptide, 24 membered cyclodepsipeptide, emodepside;

(28) Others (action mechanism is unknown): azadirachtin, benzoximate, bifenazate, bromopropylate, quinomethionate, cryolite, dicofol, pyridalyl; benclothiaz, sulfur, amidoflumet, 1, 3-dichloropropene, DCIP, phenisobromolate, benzomate, methaldehyde, chlorobenzilate, chlothiazoben, dicyclanil, fenoxacrim, fentrifanil, flubenzimine, fluphenazine, gossyplure, japonilure, metoxadiazone, oil, potassium oleate, tetrasul; triarathene; afidopyropen, flometoquin, flufiprole, fluensulfone, meperfluthrin, tetramethylfluthrin, tralopyril, dimefluthrin, methylneodecanamide; fluralaner, afoxolaner, 5-[5-(3,5-dichlorophenyl)-5-trifluoromethyl-4,5-dihydroisoxazole-3-yl]-2-(1H-1,2,4-triaz ole-1-yl)benzonitrile (CAS:943137-49-3), other meta-diamide type.
Plant growth regulators:

abscisic acid, kinetin, benzylaminopurine, 1,3-diphenylurea, forchlorfenuron, thidiazuron, chlorfenuron, dihydrozeatin, gibberelline A, gibberelline A4, gibberelline A7, gibberelline A3, 1-methylcyclopropene, N-acetyl aminoethoxyvinyl glycine (aviglycine), aminooxyacetate, silver nitrate, cobalt chloride, IAA, 4-CPA, cloprop, 2,4-D, MCPB, indole-3-butyrate, dichlorprop, phenothiol, 1-naphthyl acetamide, ethychlozate, cloxyfonac, maleic acid hydrazide, 2,3,5-triiodobenzoic acid, salicylic acid, salicylate, (−)-jasmonic acid, methyl jasmonate, (+)-strigol, (+)-deoxystrigol, (+)-orobanchol, (+)-sorgolactone, 4-oxo-4-(2-phenyl ethyl)aminobutyric acid; ethephon, chlormequat, mepiquat chloride, benzyl adenine.

The method for producing the fungicide composition of the present invention is not particularly limited. As the method for producing the fungicide composition of the present invention, for example, (a) a method of separately formulating compound A and compound B and mixing these preparations, (b) a method of formulating compound A and mixing it with compound B, (c) a method of formulating compound B and mixing it with compound A, (d) a method of mixing compound A and compound B, and optionally formulating the mixture, can be mentioned. In addition, the fungicide composition of the present invention can be made into dosage forms such as wettable powders, emulsions, powders, granules, water-soluble agents, suspensions, granules wettable powders, tablets and the like by formulation.

The concentration of the active ingredient (the total concentration of compound A and compound B) in the formulated fungicide composition of the present invention is not particularly limited, and various concentrations can be adopted depending on the dosage forms of the formulation described above. For example, in wettable powders, it is usually 5 to 90% by weight, preferably 10 to 85% by weight; in emulsions, it is usually 3 to 70% by weight, preferably 5 to 60% by weight; in granules, it is usually 0.01 to 50% by weight, preferably 0.05 to 40% by weight.

Several formulation examples are shown below. The formulations shown below are merely examples, and can be modified within a range not contrary to the essence of the present invention, and the present invention is not limited by the following formulation examples. "Part" means "part by weight" unless otherwise specified.

(Formulation 1: Wettable Powder)

| Compound A + Compound B | 40 parts |
| Diatomaceous earth | 53 parts |
| Higher alcohol sulfate | 4 parts |
| Alkyl naphthalene sulfonate | 3 parts |

The above components homogeneously mixed and finely pulverized to obtain a wettable powder containing 40% of active ingredient.

(Formulation 2: Emulsion)

| Compound A + Compound B | 30 parts |
| Xylene | 33 parts |
| Dimethylformamide | 30 parts |
| Polyoxyethylene alkyl allyl ether | 7 parts |

The above components were mixed and dissolved to obtain an emulsion containing 30% of active ingredient.

(Formulation 3: Powder)

| Compound A + Compound B | 10 parts |
| Clay | 90 parts |

The above components were homogeneously mixed and finely pulverized to obtain a powder containing 10% of active ingredient.

(Formulation 4: Granule)

| Compound A + Compound B | 5 parts |
| Clay | 73 parts |
| Bentonite | 20 parts |
| Dioctyl sulfosuccinate sodium salt | 1 part |
| Potassium phosphate | 1 part |

The above components were thoroughly pulverized and mixed, and then water is added thereto and sufficiently kneaded, followed by granulating and drying to obtain a granule containing 5% of active ingredient.

(Formulation 5: Suspension)

| Compound A + Compound B | 10 parts |
| Polyoxyethylene alkyl allyl ether | 4 parts |
| Sodium polycarboxylate | 2 parts |
| Glycerin | 10 parts |
| Xanthan gum | 0.2 part |
| Water | 73.8 parts |

The above components were mixed and wet pulverized until the particle size becomes 3 microns or less to obtain a suspension containing 10% of active ingredient.

(Formulation 6: Granular Wettable Powder)

| Compound A + Compound B | 40 parts |
| Clay | 36 parts |
| Potassium chloride | 10 parts |
| Sodium alkylbenzene sulfonate | 1 part |
| Sodium lignin sulfonate | 8 parts |
| Formaldehyde condensate of sodium alkylbenzene sulfonate | 5 parts |

The above components were homogeneously mixed and finely pulverized, followed by adding an appropriate amount of water, and kneading to a clay-like material. After granulating the clay-like material, the material was dried to obtain a water dispersible granule containing 40% of active ingredient.

The fungicide composition for agricultural and horticultural use according to the present invention may provide effects such as labor saving, by using in combination with known insecticides, acaricides, herbicides, plant growth regulators and the like.

The fungicide composition of the present invention can be used as it is or diluted to a predetermined concentration with water, or in the form of a solution, suspension or emulsion, and can be used by spraying on the plants, irrigating to the soil, mixing with the soil and spraying on the soil. In the fungicide composition of the present invention, an appropriate amount of 0.1 g or more of the active ingredient (total amount of compound A and compound B) per hectare is usually applied to the field. The fungicide composition of the present invention can also be used as a seed treating agent. It can also be used by application on water surface.

Examples of useful plants to be treated with the fungicide composition of the present invention include cereals, vegetables, root crops, potatoes, fruit trees, trees, grasses, lawn grass and the like. In the present invention, it is also possible to treat each part of these plants as a target. Examples of the each part of the plants include leaves, stems, patterns, flowers, buds, fruits, seeds, sprouts, roots, tubers, tuberous roots, shoots, cuttings and the like. It is also possible to treat improved varieties/varieties, cultivars, as well as mutants, hybrids and genetically modified organisms (GMO) of these plants.

Specific examples of useful plants are given below.

(1) Malvaceae plants, for example, okra (*Abelmoschus esculentus*) and cotton (*Gossypium hirsutum*);

(2) Sterculiaceae plants, for example, cacao (*Theobroma cacao*);

(3) Chenopodiaceae plants, for example, sugar beet (*Beta vulgaris*), Swiss chard (*Beta vulgaris* var. *cicla* L.), and spinach (*Spinacia oleracea*);

(4) Rubiaceae plants, for example, coffee (*Coffea* spp);

(5) Cannabaceae plants, for example, hop (*Humulus lupulus*)

(6) Cruciferae plants, for example, komatsuna (*Brassica cempestris*), mustard (*Brassica juncea*), tacana (*Brassica juncea* var. *integrifolia*), rape (*Brassica napus*), cauliflower (*Brassica oleracea* var. *botrytis*), cabbage (*Brassica oleracea* var. *capitata*), broccoli (*Brassica oleracea* var. *italica*), Chinese cabbage (*Brassica rapa*), bok choy (*Brassica rapa* var. *chinensis*), turnip (*Brassica rapa* var. *glabra*), Nozawana (*Brassica rapa* var. *hakabura*), mizuna (*Brassica rapa* var. *lancinifolia*), Shepherd's purse (*Capsella bursa-pastoris*), watercress (*Nasturtium* spp.), radish (*Raphanus sativus*), and wasabi (Was abia *japonica*);

(7) Linaceae plants, for example, flax (*Linaceae usitatissimum*);

(8) Gramineae plants, for example, oat (*Avena sativa*), Job's tears (*Coix lacryma-jobi* var. *ma-yuen*), orchardgrass (*Dactylis glomerata*), barley (*Hordeum vulgare*), rice (*Oryza sativa*), timothy (*TPhleum pratense*), sugar cane (*Saccharum officinarum*), rye (*Secale cereale*), millet (*Setaria italica*), bread wheat (*Triticum aestivum*), corn (*Zea mays*), and zoysiagrass (*Zoysia* spp.);

(9) Cucurbitaceae plants, for example, wax gourd (*Benincasa hispida*), watermelon (*Citrulus lanatus*), bittercup squash (*Cucurbita maxima*), Oriental pumpkin (*Cucurbita moschata*), cucurbita pepo (zucchini) (*Cucurbita pepo*), gourd (*Lagenaria siceraria*), and sponge gourd (*Luffa cylindrica*);

(10) Anacardiaceae plants, for example, cashew (*Anacardium*) and mango (*Mangifera*);

(11) Ebenaceae plants, for example, *diospyros* (*Diospyros kaki*);

(12) Betulaceae plants, for example, hazel (*Corylus avellana*);

(13) Compositae plants, for example, wormwood (*Artemisia indica* var. *maximowiczii*), burdock (*Arctium lappa* L.), chicory (*Cichorium intybus*), artichoke (*Cynara scolymus*), crown daisy (*Glebionis coronaria*), sunflower (*Helianthus annuus*), and lettuce (*Lactuca sativa*);

(14) Asparagaceae plants, for example, asparagus (*Asparagus officinalis* L.);

(15) Moraceae plants, for example, fig (*Ficus carica* L.);

(16) Juglandaceae plants, for example, walnut (*Juglans* spp.);

(17) Pedaliaceae plants, for example, sesame (*Sesamum indicum*);

(18) Piperaceae plants, for example, pepper (*Piper nigrum*);

(19) Araceae plants, for example, konjac (*Amorphophallus rivieri* var. *konjac*) and taro (*Colocasia esculenta*);

(20) Lamiaceae plants, for example, peppermint (mint) (*Mentha* spp.), basil (*Ocimum basilicum*), perilla (*Perilla frutescens* var. *crispa*), and sage (*Salvia officinalis*);

(21) Zingiberaceae plants, for example, turmeric (*Curcuma longa*), ginger (*Hedychium* spp.), and myoga (*Zingiber mioga*);

(22) Umbelliferae plants, for example, celery (*Apium graveolens* L.), carrot (*Daucus carota* var. *sativa*), seri (*Oenanthe javanica*), royal fern (*Osmunda japonica* Thunb), and parsely (*Petroselium crispum*);

(23) Grossulariaceae plants, for example, Western currant (gooseberry) (*Ribes uva-crispa*);

(24) Polygonaceae plants, for example, buckwheat (*Fagopyrum esculentum*);

(25) Ericaceae plants, for example, blueberries (*Vaccinium* spp);

(26) Theaceae plants, for example, tea plant (*Camellia sinensis*);

(27) Solanaceae plants, for example, pepper (*Capsicum annuum*), bell pepper (*Capsicum annuum* var. 'grossum'), tomato (*Lycopersicon esculentum*), tobacco (*Nicotiana tabacum*), eggplant (*Solanum melongena*), and potato (*Solanum tuberosum*);

(28) Bromeliaceae plants, for example, pineapple (*Ananas comosus*);

(29) Musaceae plants, for example, banana (*Musa* spp.);

(30) Nelumbonaceae plants, for example, lotus (*Nelumbo nucifera*)

(31) Caricaceae plants, for example, *papaya* (*Carica papaya*)

(32) Rosaceae plants, for example, quince (*Chaenomeles sinensis*), loquat (*Eriobotrya japonica* Lindl.), strawberry (*Fragaria* spp.), apple (*Malus pumila*), apricot (*Prunus armeniaca*), sweet cherry (*Prunus avium*), sour cherry (*Prunus cerasus*), almonds (*Prunus dulcis*), plum (*Prunus mume*), peach (*Prunus persica*), plum (*Prunus salicina*), pear (*Pyrus pyrifolia* var. *culta*), European pear (*Pyrus communis*), and blackberry (*Rubus* spp.);

(33) Convolvulaceae plants, for example, sweet potato (*Ipomoea batatas* Lam. var. *edulis* Makino);

(34) Vitaceae plants, for example, grape (*Vitis* spp.);

(35) Fagaceae plants, for example, chestnut (*Castanea crenata* Sieb. Et Zucc.);

(36) Actinidiaceae plants, for example, kiwi (*Actinidia deliciosa*);

(37) Leguminosae plants, for example, peanut (*Arachis hypogaea*), soybean (*Glycine max* subsp. *max*), glycine soja (*Glycine max* subsp. *soja*), lentil (*Lens culinaris*), alfalfa (*Medicago sativa*), pea legume (*Pisum sativum* L.), common bean (*Phaseolus vulgaris*), narrow-leaved vetch (*Vicia angustifolia*), broad bean (*Vicia faba*), and adzuki bean (*Vigna angularis*);

(38) Rutaceae plants, for example, yuzu (*Citrus junos*), komikan (*Kishu mandarin*) (*Citrus kinokuni*), lemon (*Citrus limon*), orange (*Citrus sinensis*), satsuma mandarin (*Citrus unshiu*), grapefruit (*Citrus×paradisi*), Kumquat (*Fortunella japonica*), and Japanese pepper (Zanthoxylum piperitum);

(39) Oleaceae plants, for example, jasmine (*Jasminum* spp.) and olive (*Olea europaea*);

(40) Dioscoreaceae plants, for example, Taiwanese yam (*Dioscorea japonica* Thunb.) and yam (*Dioscorea batatas*);

(41) Liliaceae plants, for example, onion (*Allium cepa*), leek (*Allium fistulosum*), garlic (*Allium sativum*), chives (*Allium schoenoprasum*), Chinese chive (*Allium tuberosum*), and tulip (*Tulipa gesneriana*);

The fungicide composition of the present invention can be used for controlling plant diseases derived from a wide variety of filamentous fungi, for example, fungi belong to algae fungi (Oomycetes), sac fungi (Ascomycetes), imperfect fungi (Deuteromycetes), or Basidiomycete fungi (Basidiomycetes).

Examples of plant diseases and pathogens to be controlled include the followings.

Sugar beet: brown spot disease (*Cercospora beticola*), black root disease (*Aphanomyces cochllioides*), root rot disease (*Thanatephorus cucumeris*), leaf rot disease (*Thanatephorus cucumeris*), and the like.

Peanut: brown spot disease (*Mycosphaerella arachidis*), leaf mold (*Ascochyta* sp.), rust disease (*Puccinia arachidis*), damping-off disease (*Pythium debaryanum*), rust spot disease (*Alternaria alternata*), stem rot disease (*Sclerotium rolfsii*), black rust disease (*Mycosphaerella berkeleyi*), and the like.

Cucumber: powdery mildew (*Sphaerotheca fuliginea*), downy mildew (*Pseudoperonospora cubensis*), gummy stem blight (*Mycosphaerella melonis*), wilt disease (*Fusarium oxysporum*), sclerotinia rot (*Sclerotinia sclerotiorum*), gray mold (*Botrytis cinerea*), anthracnose (*Colletotrichum orbiculare*), scab (*Cladosporium cucumerinum*), brown spot disease (*Corynespora cassicola*), damping-off disease (*Pythium debaryanam, Rhizoctonia solani* Kuhn), *Phomopsis* root rot disease (*Phomopsis* sp.), Bacterial spot (*Pseudomonas syringae* pv. *Lecrymans*), and the like.

Tomato: gray mold disease (*Botrytis cinerea*), leaf mold disease (*Cladosporium fulvum*), late blight disease (*Phytophthora infestans*), verticillium wilt disease (*Verticillium albo-atrum*), powdery mildew disease (*Oidium neolycopersici*), early blight disease (*Alternaria solani*), leaf mold disease (*Pseudocercospora fuligena*), and the like.

Eggplant: gray mold disease (*Botrytis cinerea*), black rot disease (*Corynespora melongenae*), powdery mildew disease (*Erysiphe cichoracearum*), leaf mold disease (*Mycovellosiella nattrassii*), sclerotinia rot disease (*Sclerotinia sclerotiorum*), and the like.

Strawberry: gray mold disease (*Botrytis cinerea*), powdery mildew disease (*Sohaerotheca humuli*), anthracnose disease (*Colletotrichum acutatum, Colletotrichum fragariae*), phytophthora rot disease (*Phytophthora cactorum*), soft rot disease (*Rhizopus stolonifer*), fsarium wilt disease (*Fusarium oxysporum*), and the like.

Onion: neck rot disease (*Botrytis allii*), gray mold disease (*Botrytis cinerea*), leaf blight disease (*Botrytis squamosa*), downy mildew disease (*Peronospora destructor*), *Phytophthora porri* disease (*Phytophthora porri*), and the like.

Cabbage: clubroot disease (Plasmodiophora *brassicae*), soft rot disease (*Erwinia carotovora*), black rot disease (*Xanthomonas campesrtis* pv. *campestris*), bacterial black spot disease (*Pseudomonas syringae* pv. *maculicala, Pseudomonas syringae* pv. *alisalensis*), downy mildew disease (*Peronospora parasitica*), sclerotinia rot disease (*Sclerotinia sclerotiorum*), black spot disease (*Alternaria brassicicola*), gray mold disease (*Botrytis cinerea*), and the like.

Common bean: sclerotinia rot disease (*Sclerotinia sclerotiorum*), gray mold disease (*Botrytis cinerea*), anthracnose (*Colletotrichum lindemuthianum*), angular spot disease (*Phaeoisariopsis griseola*), and the like.

Apple: powdery mildew disease (*Podosphaera leucotricha*), scab disease (*Venturia inaequalis*), Monilinia disease (*Monilinia mali*), black spot disease (*Mycosphaerella pomi*), valsa canker disease (*Valsa mali*), alternaria blotch disease (*Alternaria mali*), rust disease (*Gymnosporangium yamadae*), ring rot disease (*Botryosphaeria berengeriana*), anthracnose disease (*Glomerella cingulata, Colletotrichum acutatum*), leaf srot disease (*Diplocarpon mali*), fly speck disease (*Zygophiala jamaicensis*), Sooty blotch (*Gloeodes pomigena*), violet root rot disease (*Helicobasidium mompa*), gray mold disease (*Botrytis cinerea*), and the like.

Japanese apricot: scab disease (*Cladosporium carpophilum*), gray mold disease (*Botrytis cinerea*), brown rot disease (*Monilinia mumecola*), and the like.

Persimmon: powdery mildew disease (*Phyllactinia kakicola*), anthracnose disease (*Gloeosporium kaki*), angular leaf spot (*Cercospora kaki*), and the like.

Peach: brown rot disease (*Monilinia* fructicola), scab disease (*Cladosporium carpophilum*), phomopsis rot disease (*Phomopsis* sp.), bacterial shot hole disease (*Xanthomonas campestris* pv. *pruni*), and the like.

Almond: brown rot disease (*Monilinia laxa*), spot blotch disease (*Stigmina carpophila*), scab disease (*Cladosporium carpophilum*), red leaf spot disease (*Polystigma rubrum*), alternaria blotch disease (*Alternaria alternata*), anthracnose (*Colletotrichum* gloeospoides), and the like.

Yellow peach: brown rot disease (*Monilinia fructicola*), anthracnose disease (*Colletotrichum acutatum*), black spot disease (*Alternaria* sp.), *Monilinia Kusanoi* disease (*Monilinia kusanoi*), and the like.

Grape: gray mold disease (*Botrytis cinerea*), powdery mildew disease (*Uncinula necator*), ripe rot disease (*Glomerella cingulata, Colletotrichum acutatum*), downy mildew disease (*Plasmopara viticola*), anthracnose disease (*Elsinoe ampelina*), brown spot disease (*Pseudocercospora vitis*), black rot disease (*Guignardia bidwellii*), white rot disease (*Coniella castaneicola*), and the like.

Pear: scab disease (*Venturia nashicola*), rust disease (*Gymnosporangium asiaticum*), black spot disease (*Alternaria kikuchiana*), ring rot disease (*Botryosphaeria berengeriana*), powdery mildew disease (*Phyllactinia mali*), cytospora canker disease (*Phomopsis fukushii*), brown spot blotch disease (*Stemphylium vesicarium*), anthracnose disease (*Glomerella cingulata*), and the like.

Tea: ring spot disease (*Pestalotia theae*), anthracnose disease (*Colletotrichum* theae-*sinensis*), and the like.

Citrus fruits: scab disease (*Elsinoe fawcetti*), blue mold disease (*Penicillium italicum*), common green mold disease (*Penicillium digitatum*), gray mold disease (*Botrytis cinerea*), melanose disease (*Diaporthe citri*), canker disease (*Xanthomonas campestris* pv.*Citri*), powdery mildew disease (*Oidium* sp.), and the like.

Wheat: powdery mildew (*Erysiphe graminis* f. sp. *Tritici*), red mold disease (*Gibberella zeae*), red rust disease (*Puccinia recondita*), brown snow mold disease (*Pythium iwayamai*), pink snow mold disease (*Monographella nivalis*), eye spot disease (*Pseudocercosporella herpotrichoides*), leaf scorch disease (*Septoria tritici*), glume blotch disease (*Leptosphaeria nodorum*), typhulasnow blight disease (*Typhula incarnata*), sclerotinia snow blight disease (*Myrioscleorotinia borealis*), damping-off disease (*Gaeumanomyces graminis*), ergot disease (*Claviceps purpurea*), stinking smut disease (Tilletia caries), loose smut disease (*Ustilago nuda*), and the like.

Barley: leaf spot disease (*Pyrenophora graminea*), net blotch disease (*Pyrenophora teres*), leaf blotch disease (*Rhynchosporium secalis*), loose smut disease (*Ustilago tritici, U. nuda*), and the like.

Rice: blast disease (*Pyricularia oryzae*), sheath blight disease (*Rhizoctonia solani*), bakanae disease (*Gibberella fujikuroi*), brown spot disease (*Cochliobolus miyabeanus*), damping-off disease (*Pythium graminicolum*), bacterial leaf blight (*Xanthomonas oryzae*), bacterial seedling blight disease (*Burkholderia plantarii*), brown stripe disease (*Acidovorax avenae*), bacterial grain rot disease (*Burkholderia glumae*), Cercospora leaf spot disease (*Cercospora oryzae*), false smut disease (*Ustilaginoidea virens*), rice brown spot disease (*Alternaria alternata, Curvularia intermedia*), kernel discoloration of rice (*Alternaria padwickii*), pink coloring of rice grains (*Epicoccam purpurascenns*), and the like.

Tobacco: sclerotinia rot disease (*Sclerotinia sclerotiorum*), powdery mildew disease (*Erysiphe cichoracearum*), phytophthora rot disease (*Phytophthora nicotianae*), and the like.

Tulip: gray mold disease (*Botrytis cinerea*), and the like.

Sunflower: downy mildew disease (*Plasmopara halstedii*), sclerotinia rot disease (*Sclerotinia sclerotiorum*), and the like.

Bent grass: *Sclerotinia* snow blight (*Sclerotinia borealis*), Large patch (*Rhizoctonia solani*), Dollar spot (*Sclerotinia homoeocarpa*), blast disease (*Pyricularia* sp.), *Pythium* red blight disease (*Pythium aphanidermatum*), anthracnose disease (*Colletotrichum graminicola*), and the like.

Orchard grass: powdery mildew disease (*Erysiphe graminis*), and the like.

Soybean: purple stain disease (*Cercospora kikuchii*), downy mildew disease (*Peronospora manshurica*), phytophthora rot disease (*Phytophthora sojae*), rust disease (*Phakopsora pachyrhizi*), sclerotinia rot disease (*Sclerotinia sclerotiorum*), anthracnose disease (*Colletotrichum truncatum*), gray mold disease (*Botrytis cinerea*), and the like.

Potato: hytophthora rot disease (*Phytophthora infestans*), early blight disease (*Aleternaria solani*), scurf disease (*Thanatephorus cucumeris*), and the like.

Banana: Panama disease (*Fusarium oxysporum*), Sigatoka disease (*Mycosphaerella fijiensis, Mycosphaerella musicola*), and the like.

Rape seed: sclerotinia rot disease (*Sclerotinia sclerotiorum*), root rot disease (*Phoma lingam*), black leaf spot disease (*Alternaria brassicae*), and the like.

Coffee: rust disease (*Hemileia vastatrix*), anthracnose (*Colletotrichum coffeanum*), leaf spot disease (*Cercospora coffeicola*), and the like.

Sugarcane: brown rust disease (*Puccinia melanocephala*), and the like.

Corn: zonate spot disease (*Gloecercospora sorghi*), rust disease (*Puccinia sorghi*), southern rust disease (*Puccinia polysora*), smut disease (*Ustilago maydis*), brown spot disease (*Cochliobolus heterostrophus*), northern leaf blight (*Setophaeria turcica*), and the like.

Cotton: seedling blight disease (*Pythium* sp), rust disease (*Phakopsora gossypii*), sour rot disease (*Mycosphaerella areola*), anthracnose (*Glomerella gossypii*), and the like.

The fungicide or plant disease-controlling agent according to the present invention is an agent with low phytotoxicity, low toxicity to fish or warm-blooded animals, and is safe to use.

In addition, the fungicide composition of the present invention also has an excellent fungicidal effect against resistant fungi. Furthermore, since the effect can be exhibited at a very low dosage, the fungicide composition of the present invention has an effect of preventing appearance of new resistant fungus.

More preferred diseases to which the fungicide composition of the present invention is applied are scab disease of apple, gray mold disease of cucumber, wilt disease of cucumber, powdery mildew of wheat, red rust disease of wheat, leaf scorch disease of wheat, late blight disease of tomato, blast disease of rice, rust disease of soybean and the like.

Next, the effects of the fungicide composition of the present invention will be explained by giving test examples.

(Cucumber Gray Mold Disease Control Test)

Compound A and compound B were dissolved in an organic solvent and a surfactant to obtain an emulsion. The emulsion was diluted to a predetermined concentration with water. The diluted solution of emulsion was sprayed on the cotyledons of cucumber (variety: SHIMO SHIRAZU), and air-dried at room temperature. Subsequently, a conidia suspension of cucumber gray mold fungus (*Botrytis cinerea*) was inoculated dropwise. It was placed in a dark room at 20° C. and a high humidity for 4 days. The state of spots appeared on the leaves was compared with untreated area and the control rate was calculated. The tests were carried out in duplicate.

The theoretical control rate in the diluted solution of emulsion containing both compound A and compound B was calculated using the actual measurement control rate of the diluted solution of emulsion containing compound A alone or containing compound B alone according to Colby's formula.

$$E = M + N - MN/100$$ Colby's formula:

M: Actual measurement control rate (%) of the diluted solution of emulsion containing compound A alone N: Actual measurement control rate (%) of the diluted solution of emulsion containing compound B alone E: Theoretical control rate (%) of the diluted solution of emulsion containing both compound A and compound B The control rate of 0% means that spots of the same degree as the untreated area was observed, and the control rate of 100% means that spots were not observed.

[Chemical formula 9]

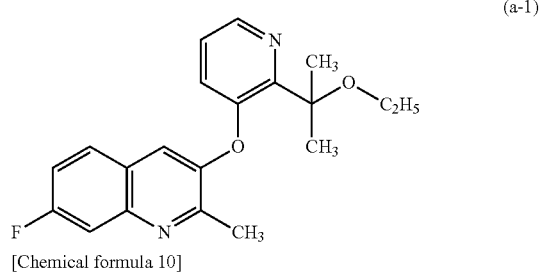

(a-1)

[Chemical formula 10]

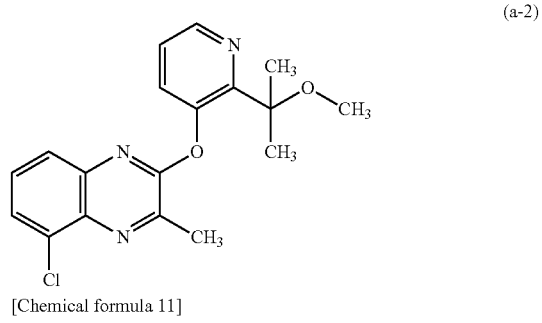

(a-2)

[Chemical formula 11]

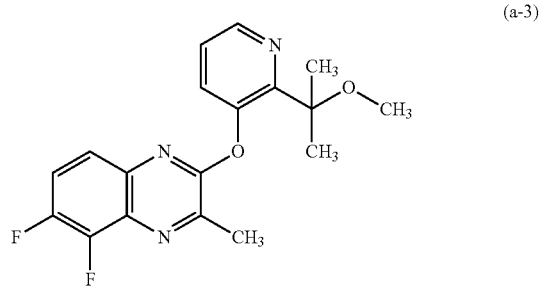

(a-3)

-continued
[Chemical formula 12]
(a-4)
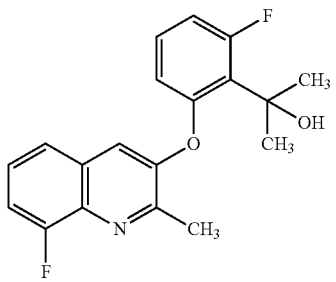
[Chemical formula 13]
(a-5)
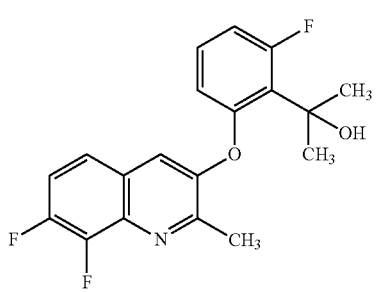
[Chemical formula 14]
(a-6)
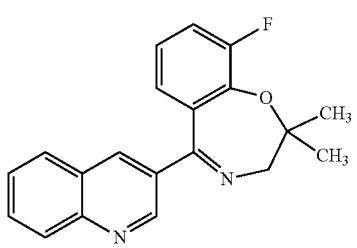
[Chemical formula 15]
(b-1)
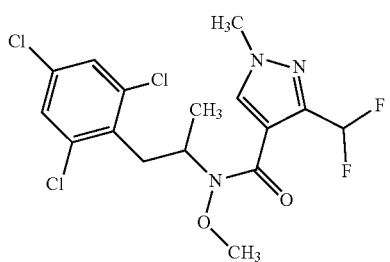
[Chemical formula 16]
(b-2)
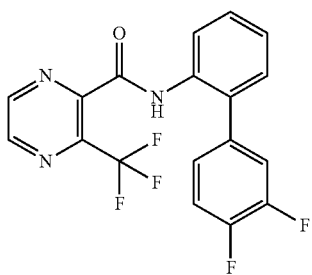
-continued
[Chemical formula 17]
(b-3)
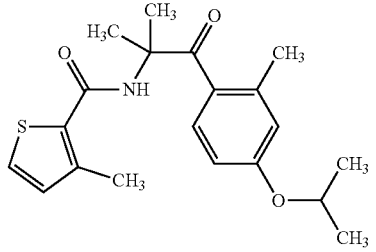
[Chemical formula 18]
(b-4)
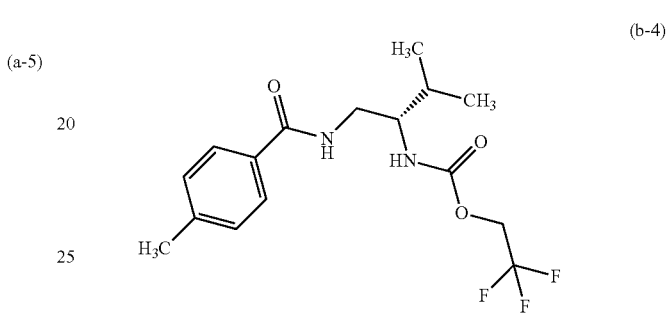
[Chemical formula 19]
(b-5)
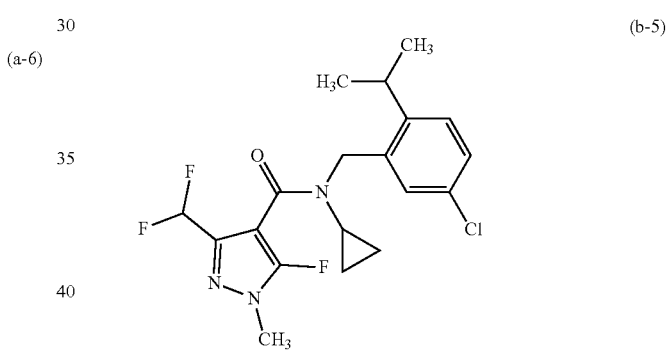
[Chemical formula 20]
(b-6)
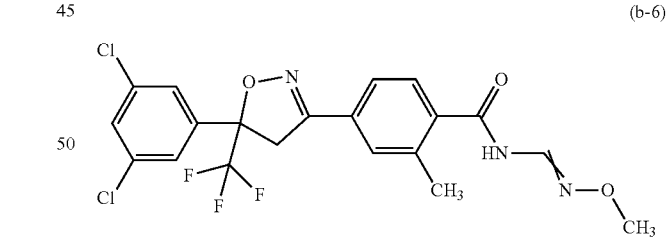
[Chemical formula 21]
(b-7)
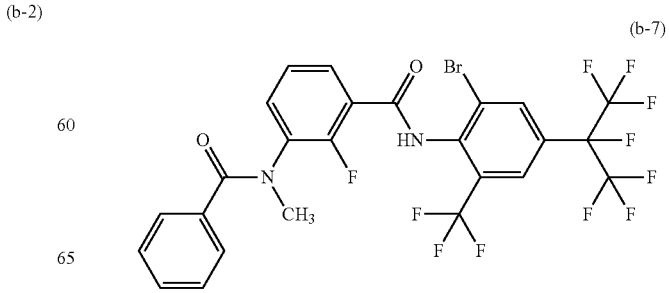

-continued

[Chemical formula 22]

(b-8)

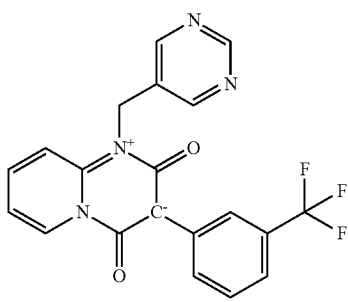

[Chemical formula 23]

(b-9)

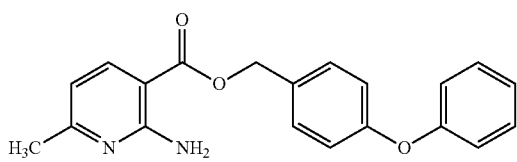

[Chemical formula 24]

(b-10)

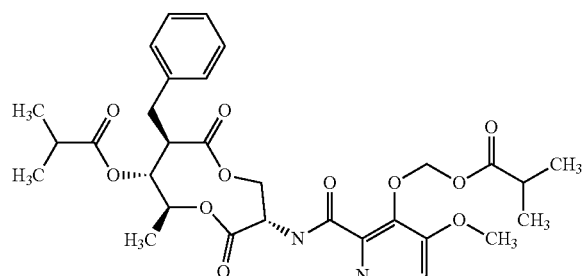

-continued

[Chemical formula 25]

(b-11)

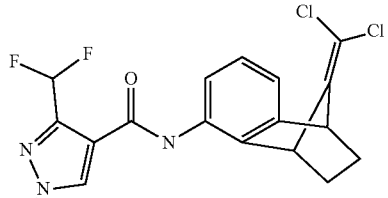

[Chemical formula 26]

(b-12)

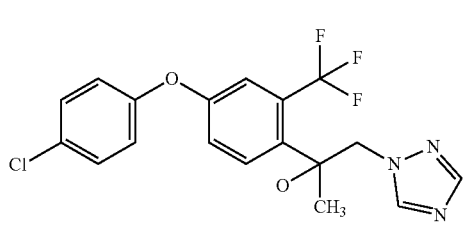

Example 1

As compound A, a compound represented by formula (a-1) was prepared. As compound B, pydiflumetofen (a compound represented by formula (b-1)), isofetamide (a compound represented by formula (b-3)), and broflanilide (a compound represented by formula (b-7)) were prepared. Cucumber gray mold disease control tests were carried out on the diluted solutions of emulsions 1a to 7a having the concentrations shown in TABLE 1. The results are shown in TABLE 1.

TABLE 1

| | Diluted solution of emulsion | | | | | | |
|---|---|---|---|---|---|---|---|
| | 1a | 2a | 3a | 4a | 5a | 6a | 7a |
| Concentration of compound A (ppm) | | | | | | | |
| a-1 | 0.1 | 0.1 | 0.1 | 0.1 | — | — | — |
| Concentration of compound B (ppm) | | | | | | | |
| b-1 | 0.4 | — | — | — | 0.4 | — | — |
| b-3 | — | 25 | — | — | — | 25 | — |
| b-7 | — | — | 100 | — | — | — | 100 |
| Actual measurement control rate (%) | 100 | 100 | 56 | 22 | 33 | 67 | 11 |
| Theoretical control rate (%) | 48 | 74 | 31 | — | — | — | — |

Example 2

As compound A, a compound represented by formula (a-1) was prepared. As compound B, pyraziflumide (a compound represented by formula (b-2)), tolprocarb (a compound represented by formula (b-4)), N-(5-chloro-2-isopropylbenzyl)-N-cyclopropyl-3-(difluoromethyl)-5-fluoro-1-methyl-1H-pyrazole-4-carboxamide (a compound represented by formula (b-5)) were prepared. Cucumber gray mold disease control tests were carried out on the diluted solutions of emulsions 8a to 15a having the concentrations shown in TABLE 2. The results are shown in TABLE 2.

TABLE 2

| | Diluted solution of emulsion | | | | | | | |
|---|---|---|---|---|---|---|---|---|
| | 8a | 9a | 10a | 11a | 12a | 13a | 14a | 15a |
| Concentration of compound A (ppm) | | | | | | | | |
| a-1 | 0.1 | 0.025 | 0.1 | 0.1 | 0.025 | — | — | — |
| Concentration of compound B(ppm) | | | | | | | | |
| b-2 | 0.4 | — | — | — | — | 0.4 | — | — |
| b-4 | — | 100 | — | — | — | — | 100 | — |
| b-5 | — | — | 6.3 | — | — | — | — | 6.3 |
| Actual measurement control rate (%) | 82 | 40 | 76 | 0 | 0 | 67 | 11 | 33 |
| Theoretical control rate (%) | 67 | 11 | 33 | — | — | — | — | — |

Example 3

As compound A, a compound represented by formula (a-1) was prepared. As compound B, fluxamethamide (a compound represented by formula (b-6)), and triflumezopyrim (a compound represented by formula (b-8)) were prepared. Cucumber gray mold disease control tests were carried out on the diluted solutions of emulsions 16a to 20a having the concentrations shown in TABLE 3. The results are shown in TABLE 3.

TABLE 3

| | Diluted solution of emulsion | | | | |
|---|---|---|---|---|---|
| | 16a | 17a | 18a | 19a | 20a |
| Concentration of compound A (ppm) | | | | | |
| a-1 | 0.1 | 0.1 | 0.1 | — | — |
| Concentration of compound B(ppm) | | | | | |
| b-6 | 200 | — | — | 200 | — |
| b-8 | — | 200 | — | — | 200 |
| Actual measurement control rate (%) | 32 | 59 | 15 | 9 | 26 |
| Theoretical control rate (%) | 23 | 39 | — | — | — |

Example 4

As compound A, a compound represented by formula (a-2) was prepared. As compound B, compounds represented by formulas (b-2), (b-3) and (b-4) were prepared. Cucumber gray mold disease control tests were carried out on the diluted solutions of emulsions 1b to 8b having the concentrations shown in TABLE 4. The results are shown in TABLE 4.

TABLE 4

| | Diluted solution of emulsion | | | | | | | |
|---|---|---|---|---|---|---|---|---|
| | 1b | 2b | 3b | 4b | 5b | 6b | 7b | 8b |
| Concentration of compound A (ppm) | | | | | | | | |
| a-2 | 0.1 | 0.025 | 0.1 | 0.025 | 0.1 | — | — | — |
| Concentration of compound B (ppm) | | | | | | | | |
| b-2 | 1.6 | — | — | — | — | 1.6 | — | — |
| b-3 | — | 6.3 | — | — | — | — | 6.3 | — |
| b-4 | — | — | 100 | — | — | — | — | 100 |
| Actual measurement control rate (%) | 100 | 100 | 44 | 11 | 22 | 82 | 33 | 11 |
| Theoretical control rate (%) | 86 | 40 | 31 | — | — | — | — | — |

Example 5

As compound A, a compound represented by formula (a-2) was prepared. As compound B, compounds represented by formulas (b-1) and (b-5) were prepared. Cucumber gray mold disease control tests were carried out on the diluted solutions of emulsions 9b to 13b having the concentrations shown in TABLE 5. The results are shown in TABLE 5.

TABLE 5

| | Diluted solution of emulsion | | | | |
|---|---|---|---|---|---|
| | 9b | 10b | 11b | 12b | 13b |
| Concentration of compound A (ppm) | | | | | |
| a-2 | 0.1 | 0.1 | 0.1 | — | — |
| Concentration of compound B (ppm) | | | | | |
| b-1 | 1.6 | — | — | 1.6 | — |
| b-5 | — | 6.3 | — | — | 6.3 |
| Actual measurement control rate (%) | 73 | 100 | 0 | 27 | 33 |
| Theoretical control rate (%) | 27 | 33 | — | — | — |

Example 6

As compound A, a compound represented by formula (a-2) was prepared. As compound B, compounds represented by formulas (b-6) and (b-7) were prepared. Cucumber gray mold disease control tests were carried out on the diluted solutions of emulsions 14b to 18b having the concentrations shown in TABLE 6. The results are shown in TABLE 6.

TABLE 6

| | Diluted solution of emulsion | | | | |
|---|---|---|---|---|---|
| | 14b | 15b | 16b | 17b | 18b |
| Concentration of compound A (ppm) | | | | | |
| a-2 | 0.025 | 0.025 | 0.025 | — | — |
| Concentration of compound B (ppm) | | | | | |
| b-6 | 200 | — | — | 200 | — |
| b-7 | — | 5 | — | — | 5 |

TABLE 6-continued

| | Diluted solution of emulsion | | | | |
|---|---|---|---|---|---|
| | 14b | 15b | 16b | 17b | 18b |
| Actual measurement control rate (%) | 76 | 71 | 21 | 59 | 47 |
| Theoretical control rate (%) | 68 | 58 | — | — | — |

Example 7

As compound A, a compound represented by formula (a-3) was prepared. As compound B, compounds represented by formulas (b-1) to (b-5) and formula (b-8) were prepared. Cucumber gray mold disease control tests were carried out on the diluted solutions of emulsions 1c to 13c having the concentrations shown in TABLE 7. The results are shown in TABLE 7.

TABLE 7

| | Diluted solution of emulsion | | | | | | |
|---|---|---|---|---|---|---|---|
| | 1c | 2c | 3c | 4c | 5c | 6c | 7c |
| Concentration of compound A (ppm) | | | | | | | |
| a-3 | 0.1 | 0.1 | 0.1 | 0.1 | 0.1 | 0.1 | 0.1 |
| Concentration of compound B (ppm) | | | | | | | |
| b-1 | 0.4 | — | — | — | — | — | — |
| b-2 | — | 1.6 | — | — | — | — | — |
| b-3 | — | — | 6.3 | — | — | — | — |
| b-4 | — | — | — | 100 | — | — | — |
| b-5 | — | — | — | — | 6.3 | — | — |
| b-8 | — | — | — | — | — | 100 | — |
| Actual measurement control rate (%) | 63 | 100 | 100 | 21 | 58 | 29 | 0 |
| Theoretical control rate (%) | 8 | 61 | 47 | 0 | 21 | 0 | — |

| | Diluted solution of emulsion | | | | | |
|---|---|---|---|---|---|---|
| | 8c | 9c | 10c | 11c | 12c | 13c |
| Concentration of compound A (ppm) | | | | | | |
| a-3 | — | — | — | — | — | — |
| Concentration of compound B (ppm) | | | | | | |
| b-1 | 0.4 | — | — | — | — | — |
| b-2 | — | 1.6 | — | — | — | — |
| b-3 | — | — | 6.3 | — | — | — |
| b-4 | — | — | — | 100 | — | — |
| b-5 | — | — | — | — | 6.3 | — |
| b-8 | — | — | — | — | — | 100 |
| Actual measurement control rate (%) | 8 | 61 | 47 | 0 | 21 | 0 |
| Theoretical control rate (%) | — | — | — | — | — | — |

Example 8

As compound A, a compound represented by formula (a-3) was prepared. As compound B, compounds represented by formulas (b-6) and (b-7) were prepared. Cucumber gray mold disease control tests were carried out on the diluted solutions of emulsions 14c to 19c having the concentrations shown in TABLE 8. The results are shown in TABLE 8.

TABLE 8

| | Diluted solution of emulsion | | | | | |
|---|---|---|---|---|---|---|
| | 14c | 15c | 16c | 17c | 18c | 19c |
| Concentration of compound A (ppm) | | | | | | |
| a-3 | 0.025 | 0.1 | 0.025 | 0.1 | — | — |

TABLE 8-continued

|  | Diluted solution of emulsion | | | | | |
|---|---|---|---|---|---|---|
|  | 14c | 15c | 16c | 17c | 18c | 19c |
| Concentration of compound B (ppm) | | | | | | |
| b-6 | 100 | — | — | — | 100 | — |
| b-7 | — | 0.31 | — | — | — | 0.31 |
| Actual measurement control rate (%) | 14 | 21 | 5 | 17 | 0 | 0 |
| Theoretical control rate (%) | 5 | 17 | — | — | — | — |

Example 9

As compound A, a compound represented by formula (a-4) was prepared. As compound B, compounds represented by formulas (b-1) to (b-4) and formulas (b-6) to (b-8) were prepared. Cucumber gray mold disease control tests were carried out on the diluted solutions of emulsions 1d to 16d having the concentrations shown in TABLE 9. The results are shown in TABLE 9.

TABLE 9

|  | Diluted solution of emulsion | | | | | | |
|---|---|---|---|---|---|---|---|
|  | 1d | 2d | 3d | 4d | 5d | 6d | 7d |
| Concentration of compound A (ppm) | | | | | | | |
| a-4 | 0.1 | 0.025 | 0.1 | 0.1 | 0.025 | 0.1 | 0.025 |
| Concentration of compound B (ppm) | | | | | | | |
| b-1 | 1.6 | — | — | — | — | — | — |
| b-2 | — | 1.6 | — | — | — | — | — |
| b-3 | — | — | 6.3 | — | — | — | — |
| b-4 | — | — | — | 100 | — | — | — |
| b-6 | — | — | — | — | 200 | — | — |
| b-7 | — | — | — | — | — | 10 | — |
| b-8 | — | — | — | — | — | — | 200 |
| Actual measurement control rate (%) | 100 | 100 | 100 | 100 | 63 | 67 | 27 |
| Theoretical control rate (%) | 58 | 40 | 35 | 3 | 17 | 19 | 0 |

|  | Diluted solution of emulsion | | | | | | | | |
|---|---|---|---|---|---|---|---|---|---|
|  | 8d | 9d | 10d | 11d | 12d | 13d | 14d | 15d | 16d |
| Concentration of compound A (ppm) | | | | | | | | | |
| a-4 | 0.1 | 0.025 | — | — | — | — | — | — | — |
| Concentration of compound B (ppm) | | | | | | | | | |
| b-1 | — | — | 1.6 | — | — | — | — | — | — |
| b-2 | — | — | — | 1.6 | — | — | — | — | — |
| b-3 | — | — | — | — | 6.3 | — | — | — | — |
| b-4 | — | — | — | — | — | 100 | — | — | — |
| b-6 | — | — | — | — | — | — | 200 | — | — |
| b-7 | — | — | — | — | — | — | — | 10 | — |
| b-8 | — | — | — | — | — | — | — | — | 200 |
| Actual measurement control rate (%) | 3 | 0 | 57 | 40 | 33 | 0 | 17 | 17 | 0 |
| Theoretical control rate (%) | — | — | — | — | — | — | — | — | — |

Example 10

As compound A, a compound represented by formula (a-4) was prepared. As compound B, a compound represented by formula (b-5) was prepared. Cucumber gray mold disease control tests were carried out on the diluted solutions of emulsions 17d to 19d having the concentrations shown in TABLE 10. The results are shown in TABLE 10.

TABLE 10

|  | Diluted solution of emulsion | | |
|---|---|---|---|
|  | 17d | 18d | 19d |
| Concentration of compound A (ppm) | | | |
| a-4 | 0.1 | 0.1 | — |

TABLE 10-continued

|  | Diluted solution of emulsion | | |
|---|---|---|---|
|  | 17d | 18d | 19d |
| Concentration of compound B (ppm) | | | |
| b-5 | 6.3 | — | 6.3 |
| Actual measurement control rate (%) | 100 | 2 | 62 |
| Theoretical control rate (%) | 63 | — | — |

Example 11

As compound A, a compound represented by formula (a-5) was prepared. As compound B, compounds represented by formulas (b-1), (b-2), (b-4), (b-5), (b-7) and (b-8) were prepared. Cucumber gray mold disease control tests were carried out on the diluted solutions of emulsions 1e to 14e having the concentrations shown in TABLE 11. The results are shown in TABLE 11.

TABLE 11

|  | Diluted solution of emulsion | | | | | |
|---|---|---|---|---|---|---|
|  | 1e | 2e | 3e | 4e | 5e | 6e |
| Concentration of compound A (ppm) | | | | | | |
| a-5 | 0.1 | 0.1 | 0.1 | 0.025 | 0.1 | 0.1 |
| Concentration of compound B (ppm) | | | | | | |
| b-1 | 0.4 | — | — | — | — | — |
| b-2 | — | 1.6 | — | — | — | — |
| b-4 | — | — | 100 | — | — | — |
| b-5 | — | — | — | 6.3 | — | — |
| b-7 | — | — | — | — | 100 | — |
| b-8 | — | — | — | — | — | 100 |
| Actual measurement control rate (%) | 69 | 100 | 86 | 100 | 86 | 83 |
| Theoretical control rate (%) | 36 | 57 | 41 | 69 | 29 | 50 |

|  | Diluted solution of emulsion | | | | | | | |
|---|---|---|---|---|---|---|---|---|
|  | 7e | 8e | 9e | 10e | 11e | 12e | 13e | 14e |
| Concentration of compound A (ppm) | | | | | | | | |
| a-5 | 0.1 | 0.025 | — | — | — | — | — | — |
| Concentration of compound B (ppm) | | | | | | | | |
| b-1 | — | — | 0.4 | — | — | — | — | — |
| b-2 | — | — | — | 1.6 | — | — | — | — |
| b-4 | — | — | — | — | 100 | — | — | — |
| b-5 | — | — | — | — | — | 6.3 | — | — |
| b-7 | — | — | — | — | — | — | 100 | — |
| b-8 | — | — | — | — | — | — | — | 100 |
| Actual measurement control rate (%) | 29 | 5 | 10 | 40 | 17 | 67 | 0 | 29 |
| Theoretical control rate (%) | — | — | — | — | — | — | — | — |

Example 12

As compound A, a compound represented by formula (a-5) was prepared. As compound B, compounds represented by formulas (b-3) and (b-6) were prepared. Cucumber gray mold disease control tests were carried out on the diluted solutions of emulsions 15e to 20e having the concentrations shown in TABLE 12. The results are shown in TABLE 12.

TABLE 12

|  | Diluted solution of emulsion | | | | | |
|---|---|---|---|---|---|---|
|  | 15e | 16e | 17e | 18e | 19e | 20e |
| Concentration of compound A (ppm) | | | | | | |
| a-5 | 0.025 | 0.1 | 0.1 | 0.025 | — | — |
| Concentration of compound B (ppm) | | | | | | |
| b-3 | 25 | — | — | — | 25 | — |
| b-6 | — | 100 | — | — | — | 100 |
| Actual measurement control rate (%) | 95 | 32 | 0 | 0 | 77 | 0 |
| Theoretical control rate (%) | 77 | 0 | — | — | — | — |

Example 13

As compound A, a compound represented by formula (a-6) was prepared. As compound B, compounds represented by formulas (b-1) to (b-8) were prepared. Cucumber gray mold disease control tests were carried out on the diluted solutions of emulsions 1f to 18f having the concentrations shown in TABLE 13. The results are shown in TABLE 13.

TABLE 13

| | Diluted solution of emulsion | | | | | | | |
|---|---|---|---|---|---|---|---|---|
| | 1f | 2f | 3f | 4f | 5f | 6f | 7f | 8f |
| Concentration of compound A (ppm) | | | | | | | | |
| a-6 | 0.025 | 0.1 | 0.1 | 0.1 | 0.1 | 0.1 | 0.1 | 0.1 |
| Concentration of compound B (ppm) | | | | | | | | |
| b-1 | 0.4 | — | — | — | — | — | — | — |
| b-2 | — | 0.4 | — | — | — | — | — | — |
| b-3 | — | — | 6.3 | — | — | — | — | — |
| b-4 | — | — | — | 100 | — | — | — | — |
| b-5 | — | — | — | — | 1.6 | — | — | — |
| b-6 | — | — | — | — | — | 200 | — | — |
| b-7 | — | — | — | — | — | — | 1.25 | — |
| b-8 | — | — | — | — | — | — | — | 200 |
| Actual measurement control rate (%) | 71 | 100 | 82 | 71 | 100 | 100 | 100 | 100 |
| Theoretical control rate (%) | 53 | 60 | 8 | 65 | 60 | 52 | 59 | 68 |

| | Diluted solution of emulsion | | | | | | | | | |
|---|---|---|---|---|---|---|---|---|---|---|
| | 9f | 10f | 11f | 12f | 13f | 14f | 15f | 16f | 17f | 18f |
| Concentration of compound A (ppm) | | | | | | | | | | |
| a-6 | 0.025 | 0.1 | — | — | — | — | — | — | — | — |
| Concentration of compound B (ppm) | | | | | | | | | | |
| b-1 | — | — | 0.4 | — | — | — | — | — | — | — |
| b-2 | — | — | — | 0.4 | — | — | — | — | — | — |
| b-3 | — | — | — | — | 6.3 | — | — | — | — | — |
| b-4 | — | — | — | — | — | 100 | — | — | — | — |
| b-5 | — | — | — | — | — | — | 1.6 | — | — | — |
| b-6 | — | — | — | — | — | — | — | 200 | — | — |
| b-7 | — | — | — | — | — | — | — | — | 1.25 | — |
| b-8 | — | — | — | — | — | — | — | — | — | 200 |
| Actual measurement control rate (%) | 0 | 39 | 53 | 34 | 8 | 42 | 34 | 21 | 32 | 47 |
| Theoretical control rate (%) | — | — | — | — | — | — | — | — | — | — |

Example 14

As compound A, a compound represented by formula (a-1) was prepared. As compound B, 4-phenoxybenzyl-2-amino-methyl nicotinate (a compound represented by formula (b-9)), fenpicoxamid (a compound represented by formula (b-10)), benzovindiflupyr (a compound represented by formula (b-11)), mefentrifluconazole (a compound represented by formula (b-12)) were prepared. Cucumber gray mold disease control tests were conducted on the diluted solutions of emulsions 21a to 30a having the concentrations shown in TABLE 14. The results are shown in TABLE 14.

TABLE 14

| | Diluted solution of emulsion | | | | | | | | | |
|---|---|---|---|---|---|---|---|---|---|---|
| | 21a | 22a | 23a | 24a | 25a | 26a | 27a | 28a | 29a | 30a |
| Concentration of compound A (ppm) | | | | | | | | | | |
| a-1 | 1.6 | 0.4 | 1.6 | 1.6 | 1.6 | 0.4 | — | — | — | — |
| Concentration of compound B (ppm) | | | | | | | | | | |
| b-9 | 1.6 | — | — | — | — | — | 1.6 | — | — | — |
| b-10 | — | 1.6 | — | — | — | — | — | 1.6 | — | — |
| b-11 | — | — | 6.3 | — | — | — | — | — | 6.3 | — |
| b-12 | — | — | — | 6.3 | — | — | — | — | — | 6.3 |

TABLE 14-continued

| | Diluted solution of emulsion | | | | | | | | | |
|---|---|---|---|---|---|---|---|---|---|---|
| | 21a | 22a | 23a | 24a | 25a | 26a | 27a | 28a | 29a | 30a |
| Actual measurement control rate (%) | 92 | 81 | 88 | 89 | 73 | 28 | 25 | 54 | 38 | 53 |
| Theoretical control rate (%) | 80 | 67 | 83 | 87 | — | — | — | — | — | — |

Example 15

As compound A, a compound represented by formula (a-2) was prepared. As compound B, compounds represented by formulas (b-9) to (b-12) were prepared. Cucumber gray mold disease control tests were carried out on the diluted solutions of emulsions 19b to 28b having the concentrations shown in TABLE 15. The results are shown in TABLE 15.

TABLE 15

| | Diluted solution of emulsion | | | | | | | | | |
|---|---|---|---|---|---|---|---|---|---|---|
| | 19b | 20b | 21b | 22b | 23b | 24b | 25b | 26b | 27b | 28b |
| Concentration of compound A(ppm) | | | | | | | | | | |
| a-2 | 1.6 | 0.4 | 1.6 | 1.6 | 1.6 | 0.4 | — | — | — | — |
| Concentration of compound B (ppm) | | | | | | | | | | |
| b-9 | 1.6 | — | — | — | — | — | 1.6 | — | — | — |
| b-10 | — | 1.6 | — | — | — | — | — | 1.6 | — | — |
| b-11 | — | — | 1.6 | — | — | — | — | — | 1.6 | — |
| b-12 | — | — | — | 6.3 | — | — | — | — | — | 6.3 |
| Actual measurement control rate (%) | 100 | 91 | 100 | 89 | 75 | 36 | 25 | 54 | 19 | 53 |
| Theoretical control rate (%) | 81 | 71 | 80 | 88 | — | — | — | — | — | — |

Example 16

As compound A, a compound represented by formula (a-3) was prepared. As compound B, compounds represented by formulas (b-9) to (b-12) were prepared. Cucumber gray mold disease control tests were carried out on the diluted solutions of emulsions 20c to 28c having the concentrations shown in TABLE 16. The results are shown in TABLE 16.

TABLE 16

| | Diluted solution of emulsion | | | | | | | | |
|---|---|---|---|---|---|---|---|---|---|
| | 20c | 21c | 22c | 23c | 24c | 25c | 26c | 27c | 28c |
| Concentration of compound A(ppm) | | | | | | | | | |
| a-3 | 1.6 | 1.6 | 1.6 | 1.6 | 1.6 | — | — | — | — |
| Concentration of compound B (ppm) | | | | | | | | | |
| b-9 | 1.6 | — | — | — | — | 1.6 | — | — | — |
| b-10 | — | 6.3 | — | — | — | — | 6.3 | — | — |
| b-11 | — | — | 6.3 | — | — | — | — | 6.3 | — |
| b-12 | — | — | — | 6.3 | — | — | — | — | 6.3 |
| Actual measurement control rate (%) | 100 | 91 | 84 | 91 | 71 | 25 | 50 | 38 | 53 |
| Theoretical control rate (%) | 78 | 86 | 82 | 86 | — | — | — | — | — |

Example 17

As compound A, a compound represented by formula (a-4) was prepared. As compound B, compounds represented by formulas (b-9) to (b-12) were prepared. Cucumber gray mold disease control tests were carried out on the diluted solutions of emulsions 20d to 28d having the concentrations shown in TABLE 17. The results are shown in TABLE 17.

TABLE 17

| | Diluted solution of emulsion | | | | | | | | |
|---|---|---|---|---|---|---|---|---|---|
| | 20d | 21d | 22d | 23d | 24d | 25d | 26d | 27d | 28d |
| Concentration of compound A(ppm) | | | | | | | | | |
| a-4 | 1.6 | 1.6 | 1.6 | 1.6 | 1.6 | — | — | — | — |
| Concentration of compound B (ppm) | | | | | | | | | |
| b-9 | 1.6 | — | — | — | — | 1.6 | — | — | — |
| b-10 | — | 1.6 | — | — | — | — | 1.6 | — | — |
| b-11 | — | — | 6.3 | — | — | — | — | 6.3 | — |
| b-12 | — | — | — | 1.6 | — | — | — | — | 1.6 |
| Actual measurement control rate (%) | 86 | 91 | 88 | 83 | 72 | 25 | 54 | 38 | 19 |
| Theoretical control rate (%) | 79 | 87 | 83 | 77 | — | — | — | — | — |

Example 18

As compound A, a compound represented by formula (a-5) was prepared. As compound B, compounds represented by formulas (b-9) to (b-12) were prepared. Cucumber gray mold disease control tests were carried out on the diluted solutions of emulsions 21e to 30e having the concentrations shown in TABLE 18. The results are shown in TABLE 18.

TABLE 18

| | Diluted solution of emulsion | | | | | | | | | |
|---|---|---|---|---|---|---|---|---|---|---|
| | 21e | 22e | 23e | 24e | 25e | 26e | 27e | 28e | 29e | 30e |
| Concentration of compound A(ppm) | | | | | | | | | | |
| a-5 | 1.6 | 0.4 | 1.6 | 1.6 | 1.6 | 0.4 | — | — | — | — |
| Concentration of compound B (ppm) | | | | | | | | | | |
| b-9 | 1.6 | — | — | — | — | — | 1.6 | — | — | — |
| b-10 | — | 1.6 | — | — | — | — | — | 1.6 | — | — |
| b-11 | — | — | 1.6 | — | — | — | — | — | 1.6 | — |
| b-12 | — | — | — | 6.3 | — | — | — | — | — | 6.3 |
| Actual measurement control rate (%) | 100 | 91 | 100 | 89 | 75 | 36 | 25 | 54 | 19 | 53 |
| Theoretical control rate (%) | 81 | 71 | 80 | 88 | — | — | — | — | — | — |

Example 19

As compound A, a compound represented by formula (a-6) was prepared. As compound B, compounds represented by formulas (b-9) to (b-12) were prepared. Cucumber gray mold disease control tests were carried out on the diluted solutions of emulsions 19f to 27f having the concentrations shown in TABLE 19. The results are shown in TABLE 19.

TABLE 23

| | Diluted solution of emulsion | | | | | | | | |
|---|---|---|---|---|---|---|---|---|---|
| | 19f | 20f | 21f | 22f | 23f | 24f | 25f | 26f | 27f |
| Concentration of compound A (ppm) | | | | | | | | | |
| a-6 | 1.6 | 1.6 | 1.6 | 1.6 | 1.6 | — | — | — | — |
| Concentration of compound B (ppm) | | | | | | | | | |
| b-9 | 1.6 | — | — | — | — | 1.6 | — | — | — |
| b-10 | — | 6.3 | — | — | — | — | 6.3 | — | — |
| b-11 | — | — | 1.6 | — | — | — | — | 1.6 | — |
| b-12 | — | — | — | 1.6 | — | — | — | — | 1.6 |
| Actual measurement control rate (%) | 99 | 99 | 88 | 90 | 82 | 25 | 50 | 19 | 19 |
| Theoretical control rate (%) | 87 | 91 | 85 | 85 | — | — | — | — | — |

As shown in the above tables, the actual control rate in the case of using the fungicide composition of the present invention exceeds the theoretical control rate calculated according to the above-mentioned Colby's equation. All of the fungicide compositions of the present invention exhibit a synergistic fungicidal effect.

INDUSTRIAL APPLICABILITY

The fungicide composition for agricultural and horticultural use according to the present invention exhibits an excellent controlling effect against plant diseases even at a very low dosage and is free from concerns about phytotoxicity to useful plants. Further, the fungicide composition for agricultural and horticultural use according to the present invention exhibits a remarkable synergistic plant disease control effect that cannot be predicted from the plant disease control effect obtained when using compound A alone or compound B alone. Therefore, the present invention is industrially useful.

The invention claimed is:

1. A fungicide composition for agricultural and horticultural use comprising:
   at least one compound A selected from the group consisting of a compound represented by formula (1), and salts thereof; and
   at least one compound B selected from the group consisting of pyraziflumid, isofetamid, tolprocarb, fluxametamide, broflanilide, triflumezopyrim, tiadinil, fenoxanil, 4 phenoxybenzyl 2-amino-6-methyl nicotinate, fenpicoxamid, benzovindiflupyr, mefentrifluconazole, mandestrobin, and dichlobentiazox,

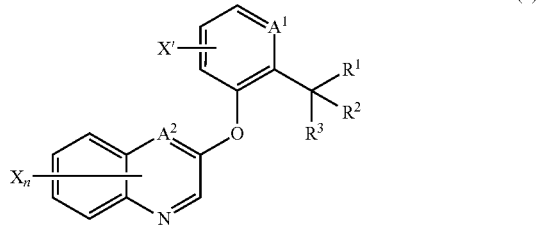

(1)

in formula (1), X each independently represents a halogeno group or a C1-6 alkyl group, n represents a number of X and is an integer of 0 to 5, X' represents a halogeno group, $R^1$, $R^2$ and $R^3$ each independently represents a C1-6 alkyl group, a C1-6 alkoxy group or a hydroxyl group, $A^1$ is a nitrogen atom, CH or CX, and $A^2$ is CH or CX.

2. A fungicide composition for agricultural and horticultural use comprising a compound represented by formula (a-1);

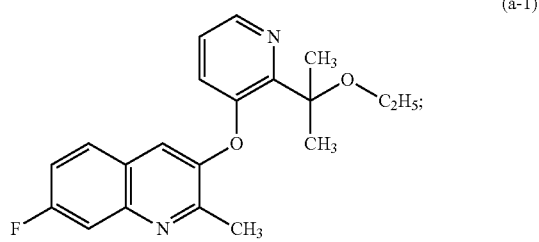

(a-1)

and at least one compound B selected from the group consisting of pyraziflumid, isofetamid, tolprocarb, fluxametamide, broflanilide, triflumezopyrim, tiadinil, fenoxanil, 4-phenoxybenzyl 2-amino-6-methyl nicotinate, fenpicoxamid, benzovindiflupyr, mefentrifluconazole, mandestrobin and dichlobentiazox.

3. The fungicide composition for agricultural and horticultural use according to claim 1, wherein compound A is a compound represented by formula (a-4)

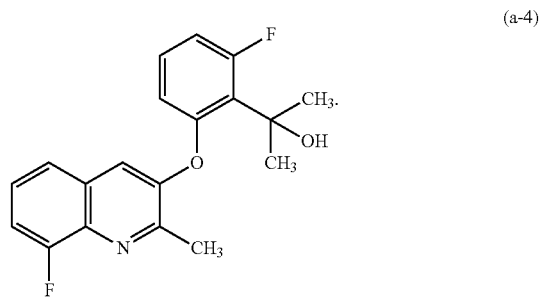 [SMILES: Cc1nc2c(F)cccc2cc1Oc1cccc(F)c1C(C)(C)O]

(a-4)

4. The fungicide composition for agricultural and horticultural use according to claim 1, wherein compound A is a compound represented by formula (a-5)

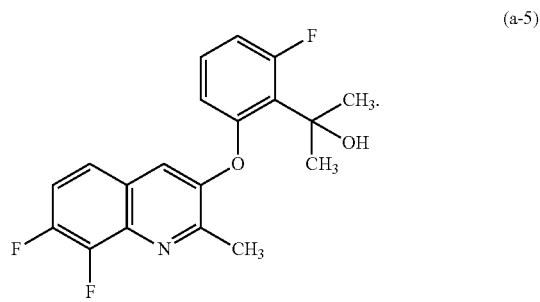 [SMILES: Cc1nc2c(F)c(F)ccc2cc1Oc1cccc(F)c1C(C)(C)O]

(a-5)

5. The fungicide composition for agricultural and horticultural use according to claim 1, wherein compound B is at least one selected from the group consisting of pyraziflumid, isofetamid, tolprocarb, fluxametamide, broflanilide, triflumezopyrim, 4-phenoxybenzyl 2-amino-6-methyl nicotinate, fenpicoxamid, benzovindiflupyr and mefentrifluconazole.

6. The fungicide composition for agricultural and horticultural use according to claim 1, wherein compound B is at least one selected from the group consisting of pyraziflumid, tolprocarb, fluxametamide, triflumezopyrim, 4-phenoxybenzyl 2-amino-6-methyl nicotinate, fenpicoxamid and benzovindiflupyr.

7. The fungicide composition for agricultural and horticultural use according to claim 1, wherein compound B is at least one selected from the group consisting of pyraziflumid, tolprocarb, 4-phenoxybenzyl 2-amino-6-methyl nicotinate, fenpicoxamid and benzovindiflupyr.

8. The fungicide composition for agricultural and horticultural use according to claim 1, wherein $A^1$ represents CH or CX.

* * * * *